US007943632B2

(12) United States Patent
Katzman et al.

(10) Patent No.: US 7,943,632 B2
(45) Date of Patent: May 17, 2011

(54) HIGH POTENCY DOPAMINERGIC TREATMENT OF NEUROLOGICAL IMPAIRMENT ASSOCIATED WITH BRAIN INJURY

(75) Inventors: Daniel E. Katzman, Newton, MA (US); Elkan R. Gamzu, Newton, MA (US); Neal M. Farber, Waban, MA (US); Esteban A. Fridman, Capital Federal (AR); Marcelo Merello, Capital Federal (AR)

(73) Assignee: NeuroHealing Pharmaceuticals, Inc., Newton, MA (US)

( * ) Notice: Subject to any disclaimer, the term of this patent is extended or adjusted under 35 U.S.C. 154(b) by 1621 days.

(21) Appl. No.: 11/240,281

(22) Filed: Sep. 30, 2005

(65) Prior Publication Data
US 2006/0089373 A1  Apr. 27, 2006

Related U.S. Application Data

(63) Continuation-in-part of application No. 10/549,489, filed as application No. PCT/US2004/008120 on Mar. 17, 2004, now abandoned.

(60) Provisional application No. 60/455,405, filed on Mar. 17, 2003, provisional application No. 60/653,619, filed on Feb. 16, 2005.

(51) Int. Cl.
*A61K 31/44* (2006.01)
*A61K 31/195* (2006.01)
(52) U.S. Cl. ................................ 514/284; 514/567
(58) Field of Classification Search ................ 514/284, 514/567
See application file for complete search history.

(56) References Cited

U.S. PATENT DOCUMENTS

| 3,961,060 | A | | 6/1976 | Fuxe |
| 5,770,606 | A | | 6/1998 | El-Rashidy et al. |
| 5,858,024 | A | * | 1/1999 | De Lacharriere et al. ........ 8/408 |
| 5,957,873 | A | * | 9/1999 | Allen ........................... 602/19 |
| 6,306,437 | B1 | | 10/2001 | El-Rashidy et al. |
| 6,310,085 | B1 | | 10/2001 | Willis |
| 6,436,950 | B1 | | 8/2002 | Achari et al. |
| 6,463,328 | B1 | | 10/2002 | John |
| 6,492,396 | B2 | * | 12/2002 | Bacon et al. .................. 514/332 |

OTHER PUBLICATIONS

International Preliminary Report on Patentability (IPRP) for international application No. PCT/US04/08120 (Oct. 6, 2005).
Written Opinion of the International Searching Authority for international application No. PCT/US04/08120 (Oct. 25, 2004).
International Search Report for international application No. PCT/US04/08120 (Oct. 25, 2004).
Supplementary European Search Report for European patent application No. 04757552 (Nov. 18, 2008).
Haig et al., *Arch. Phys. Med. Rehab. II*, 71: 1081-1083 (1990) (from Suppl. European Search Report).
Mitchell et al., *Brain Injury*, 4(3): 273-279 (1990) (from Suppl. European Search Report).
Tang et al., *European Journal of Neuroscience*, 9: 1720-1727 (1997) (from Suppl. European Search Report).
Velluz, J., *Revue Du Corps De Sante Militaire*, 8(2): 275-282 (1952) (abstract) (from Suppl. European Search Report).
Ashwal, *Brain & Develp.*, 25: 535-545 (2003).
Colosimo et al., *Clin. Neuropharmocol.*, 17(3): 243-259 (1994).
Giacino et al., *Arch. Phys. Med. Rehahbil.*, 72: 897-901 (1991).
Giacino et al., *JFK Coma Recovery Scale and Coma Intervention Program Treatment Procedures*, (Center for Head Injuries, JFK Johnson Rehabilitation Institute, Edison, New Jersey), pp. 1-25 (1992).
Giacino et al., *Neurology*, 58: 349-353 (2002).
Haig et al., *Arch. Phys. Med. Rehabil.*, 71: 1081-1083 (1990).
Jennet et al., *Lancet*, 1: 480-484 (1975).
Lees et al., *Fund. Clin. Pharmacol.*, 7: 121-128 (1993).
Meythaler et al., *J. Head Trauma Rehabil.*, 17(4): 300-313 (2002).
Missale et al., *Physiol. Rev.*, 78(1): 189-216 (1998).
Nicolle et al., *Fund. Clin. Pharmacol.*, 7: 245-252 (1993).
O'Dell et al., *Neurorehabil.*, 6: 45-55 (1996).
Passler et al., *Arch. Phys. Med. Rehabil.*, 82: 311-315 (2001).
Pilon et al., *Brain Injury*, 10(6): 421-437 (1996).
Rappaport et al., *Arch. Phys. Med. Rehabil.*, 63: 118-123 (1982).
Rappaport et al., *Arch. Phys. Med. Rehabil.*, 73: 628-634 (1992).
Spiridonov V.K. et al., *Activity of dopaminergic terminals of rat forebrain nuclei during electroconvulsive amnesia and reproduction of conditioned reaction of "Passive" avoidance restored with apomorphine*, 31(2): 409-411 (1981)(Russian document and English translation enclosed).
Talbot et al., *Brain Injury*, 8(8): 689-699 (1994).
Whyte et al., *J. Head Trauma Rehabil.*, 17(4): 284-299 (2002).
Wilson et al., *J. Neurotrauma*, 15(8): 573-585 (1998).
Wolf et al., *Brain Injury*, 9(5): 487-493 (1995).
Zafonte et al., *J. Head Trauma Rehabil.*, 15(5): 1179-1182 (2000).
Ashwal, *Brain & Development*, 25: 535-545 (2003).
Colosimo et al., *Clinical Neuropharmacology*, 17(3): 243-259 (1994).
Giacino et al., JFK Coma Recovery Scale and Coma Intervention Program Treatment Procedures, (Center for Head Injuries, JFK Johnson Rehabilitation Institute, Edison, New Jersey) p. 1-25 (1992).

(Continued)

*Primary Examiner* — Kevin Weddington
(74) *Attorney, Agent, or Firm* — Leon R. Yankwich; David G. O'Brien; Yankwich & Associates, P.C.

(57) ABSTRACT

Methods and compositions are described for treating impaired neurological function, including altered state of consciousness disorders, in an individual who has sustained a brain injury comprising administering to the individual apomorphine. Methods and compositions are described for treating impaired neurological function, including altered state of consciousness disorders, in an individual who has sustained a brain injury comprising administering to the individual at least 1000 mg or more of L-dopa (levodopa) per day. The use of potent dopaminergic agents to stimulate emergence from an altered consciousness state, such as a coma, is disclosed.

43 Claims, 2 Drawing Sheets

OTHER PUBLICATIONS

Giacino et al., *American Academy of Neurolgy*, 58: 349-353 (2002).
Giacino et al., *Arch. Phys. Med. Rehabil.*, 72: 897-901 (1991).
Haig et al., *Arch. Phys. Med. Rehabil.*, 71: 1081-1083 (1990).
Jennet et al., *The Lancet*, 1: 480-484 (1975).
Kaplan et al., *Clinical Neurology and Neurosurgery*, 105: 153-155 (2003).
Lees AJ, *Fundam. Clin. Pharmacol.*, 7: 121-128 (1993).
Meythaler et al., *J. Head Trauma Rehabil.*, 17(4): 300-313 (2002).
Missale et al., *Physiological Reviews*, 78(1): 189-225 (1998).
Nicolle et al., *Fundam. Clin. Pharmacol.*, 7: 245-252 (1993).
Passler et al., *Arch. Phys. Med. Rehab.*, 82: 311-315 (2001).
Pilon et al., *Brain Injury*, 10(6): 421-437 (1996).
Rappaport et al., *Arch. Phys. Med. Rehabil.*, 63: 118-123 (1982).
Rappaport et al., *Arch. Phys. Med. Rehabil.*, 73: 628-634 (1992).
Spiridonov et al., *Zh. vysshei nerv. deiat. Pavlova*, 31(2): 409-411 (1981) (in Russian with English translation attached).
Talbot et al., *Brain Injury*, 8(8): 689-699 (1994).
van Woerkom et al., *Eur. Neurol.*, 21: 227-234 (1982).
Whyte et al., *J. Head Trauma Rehabil.*, 17(4): 284-299 (2002).
Wilson et al., *Journal of Neurotrauma*, 15(8): 573-585 (1998).
Wolf et al., *Brain Injury*, 9(5): 487-493 (1995).
Zafonte et al., *J. Head Trauma Rehabil.*, 15(5): 1179-1182 (2000).
The Multi-Society Task Force on Persistent Vegetative State (PVS), *N. Engl. J. Med.*, 330(21): 1499-1508 (1994).
The Multi-Society Task Force on PVS, *N. Engl. J. Med.*, 330(22): 1572-1579 (1994).

* cited by examiner

HIGH POTENCY DOPAMINERGIC TREATMENT OF NEUROLOGICAL IMPAIRMENT ASSOCIATED WITH BRAIN INJURY

CROSS-REFERENCE TO RELATED APPLICATIONS

This application is a continuation-in-part of U.S. application Ser. No. 10/549,489, filed Sep. 15, 2005, now abandoned, under 35 U.S.C. §371, as the U.S. national stage of international application No. PCT/US2004/008120, filed Mar. 17, 2004, which claims the benefit of U.S. Provisional No. 60/455,405, filed Mar. 17, 2003, and this application also claims the benefit of U.S. Provisional Application No. 60/653,619, filed Feb. 16, 2005.

FIELD OF THE INVENTION

This invention is related to the fields of neurology and neurorehabilitation. In particular, this invention is related to treatments to restore impaired neurological function associated with brain injury in an individual.

BACKGROUND OF THE INVENTION

There are approximately 1.5 million new cases of head injuries to people in the United States every year. Of these, about 300,000 are severe enough to require hospitalization, and 50,000 to 75,000 will result in a coma that lasts for more than two weeks. Due to constant advances in effective emergency medicine, many patients that sustain a brain injury due to any of a variety of trauma will survive but remain in a severe altered state of consciousness, such as a coma, the deepest state of unconsciousness, or another more emergent but altered state of consciousness, such as persistent vegetative state (PVS) or minimally conscious state (MCS). Such patients fail to emerge to the fully, functional state of awareness of self and environment that they possessed prior to brain injury. Occasionally, some patients may emerge from a particular, deeper state of altered consciousness to a higher state, or even to normal awareness. However, even with emergence to full awareness, it is not uncommon for such individuals to require some form of neurorehabilitation to improve or regain any of a number of neurological functions, such as communication skills, motor skills, memory skills, and various other cognitive functions that permit self care, mobility, and employability. Clearly, patients that are in or have emerged from a severely altered state of consciousness represent a significant emotional, social, and economic burden to their families and to society.

Different therapeutic interventions have been proposed to aid the functional recovery of post-traumatic coma patients, but the results have been inconclusive. There have been a few case reports describing the use of different pharmacological agents on post-traumatic coma patients, e.g., using oral formulations of levodopa and carbidopa (Haig et al., *Arch. Phys. Med Rehabil.*, 71: 1081-1083 (1990)), bromocriptine (Passler et al., *Arch. Phys. Med. Rehab.*, 82: 311-315 (2001)), methylphenidate (Whyte et al., *J. Head Trauma Rehabil.*, 17(4): 284-299 (2002)), and amantidine (Wolf and Gleckman, *Brain Injury*, 9(5): 487-493 (1995); Meythaler et al., *J. Head Trauma Rehabil.*, 17(1): 300-314 (2002)). The need for innovative clinical research on coma and other altered states of consciousness disorders has never been greater, since relatively recent advances in medicine have enabled survival of a higher percentage of patients of head injury. Yet, there are no generally accepted therapeutic options to promote emergence from an altered state of consciousness or to stimulate neurorehabilitation of patients of brain injuries.

It has been suggested that coma duration is directly related to functional recovery as measured by any of a variety of disability scales used to assess patients, i.e., the longer a patient remains in an altered state of consciousness, the longer the patient requires some form of neurorehabilitative treatment. Such neurorehabilitative treatments may not only have the goal of restoring a patient with brain injury to a higher, preferably normal state of consciousness but also to restore or improve any of a variety of neurological functions that may have been impaired due to the brain injury, such as, communication skills (speaking, writing), cognitive skills (e.g., reasoning, memory), and motor skills (directed movements, walking, running, balancing). In addition, in recent years, important new findings have been made that indicate an ability of the neural network of the brain of a trauma patient to reorganize itself, a mechanism known variously as "neural plasticity", "axonal plasticity", "adaptive plasticity", or "activity-dependent plasticity", in which interactions between surviving neurons may adopt a new function or be recruited to restore a lost neurological function. A treatment that promotes a patient's emergence to a greater state of awareness should, in theory, also expedite the neurorehabilitation process. Clearly, needs remain for effective therapies to treat impaired neurological function in patients that have suffered brain injury.

SUMMARY OF THE INVENTION

The invention described herein addresses the above needs and problems by providing methods and means for treating one or a combination of impaired neurological functions in individuals who have sustained a brain injury, comprising administering to the individual a high potency dopaminergic agent. Impaired neurological functions treated according to the invention are the result of an injury to the brain, such as may arise from traumatic brain injury (e.g., resulting from a fall on a hard surface or vehicle accident, a strike to the head), an ischemic event (e.g., stroke), anoxic event, hypoxic event, a drug-induced injury (e.g., anesthesia-induced, drug overdose, illicit drug use), or as a result of major organ failure.

Impaired neurological function associated with brain injury that may be treated with methods and compositions according to the invention include, but are not limited to, a less than normal state of consciousness (e.g., coma, near-coma, vegetative state, persistent vegetative state, minimally conscious state) and/or other impaired functions that are primarily cognitive functions (e.g., in addition to state of consciousness, aspects of memory, voice recognition), primarily sensory functions (e.g., tactile sensing, hot-cold sensing, light sensing), primarily motor functions (e.g., directed body movements, walking, maintaining balance), or a combination of (complex or integrated) neurological functions (e.g., speaking, writing, use of tools, operating machines).

The invention provides methods for treating one or more impaired neurological functions associated with a brain injury in an individual comprising administering to the individual an effective amount of the highly potent dopaminergic agent apomorphine.

In a preferred embodiment, apomorphine is administered to an individual according to the invention at a dose in the range of from 24 to 200 mg of apomorphine per day (mg/day), more preferably, 48-128 mg/day. Daily dosing may be accomplished by single, multiple, or continuous injection or infusion of apomorphine into an individual. A preferred regimen for administering apomorphine to an individual according to the invention is to administer apomorphine at a rate of from 2 to 8 mg per hour for 12 to 16 hours per day.

Preferably, treatments according to the invention are applied to an individual for no longer than 18 to 24 months; more preferably, no longer than 12 to 18 months; more preferably, no longer than 6 to 12 months; most preferably no longer than 6 to 26 weeks. Treatments described herein may be applied to an individual more than once, e.g., after a pause or hiatus.

Methods of the invention may also comprise administering apomorphine to an individual in conjunction (e.g., co-administration, concurrent administration, sequential administration) with one or more other compounds that may provide additional therapeutic benefits, including, without limitation, anti-emetic agents and/or other dopaminergic agents. It is understood that various compounds may be administered to an individual in a mixture with apomorphine or separately, at the same time or different times (e.g., sequentially) as administering apomorphine, and/or by the same or different route as used for administering apomorphine.

Preferred anti-emetic agents useful in the invention include, but are not limited to, peripheral dopamine antagonists, phenothiazine agents, benzamide agents, serotonin antagonists, histamine antagonists (antihistamines), parasympathetic depressants, and meclizine agents. Other anti-emetic agents that can be used in accordance with the present invention include metoclopramide; phenothiazines such as chlorpromazine, prochlorperazine, pipamazine, thiethylperazine and oxypendyl hydrochloride; serotonin (5-hydroxytryptamine or 5-IIT) agonists such as domperidone, odansetron; histamine antagonists including buclizine hydrochloride, cyclizine hydrochloride, and dimenhydrinate; parasympathetic depressants such as scopolamine; metopimazine; trimethobenzamide; benzquinamine hydrochloride; and diphenidol hydrochloride. Particularly useful anti-emetic agents are trimethobenzamide hydrochloride and domperidone. An anti-emetic agent is preferably, although not necessarily, administered to an individual prior to administration of apomorphine.

Any of a variety of dopaminergic agents may be administered to an individual according to the invention including, but not limited to, L-dopa (levodopa), bromocriptine, amantadine, pergolide, pramipexole, ropinirole, fenoldopam, cabergoline, rotigotine, lysuride, talipexale, 7-OH DPAT, quinpirole, SKF-38393, and combinations thereof. When apomorphine is administered to an individual in conjunction with L-dopa according to the invention, the concentration of L-dopa may be similar to or less than the relatively high concentrations (e.g., 1000 mg or more per day) that are used in other embodiments of the invention that employ L-dopa as the primary or only high potency dopaminergic agent to treat impaired neurological function(s) associated with a brain injury in an individual (see, below).

In still another embodiment of the invention, apomorphine may be administered to an individual to treat an impaired neurological function(s) in conjunction with any of a variety of neurorehabilitation programs for restoring neurological function. Neurorehabilitation programs useful in the invention include, without limitation, physical/sensory type protocols (exercises, tasks, light stimulation, voice stimulation, pictures, tactile stimulation), electric and/or magnetic stimulation regimens (e.g., trans-cranial magnetic stimulation (TMS), deep brain stimulation (DBS)), drug-based enhancement or stimulation regimens (e.g., using modafinil, caffeine, amphetamines), and combinations thereof.

In another embodiment of the invention, apomorphine is administered to an individual parenterally (i.e., by a route outside the alimentary canal), including, without limitation, subcutaneously (s.c.), intravenously (i.v.), intramuscularly (i.m.), intra-arteriorally (i.a.) and intra-nasally (i.n.). In a preferred embodiment, apomorphine is formulated for and administered subcutaneously for use according to the invention. Apomorphine may be advantageously administered manually or automatically via a medical device, such as a pump.

In another embodiment, the invention provides methods and compositions for treating an impaired neurological function in an individual who has sustained a brain injury comprising administering to the individual at least 1000 mg/day of L-dopa (levodopa), which is a dopamine precursor that is metabolized in vivo to the neurotransmitter dopamine. At such doses, L-dopa is an effective high potency dopaminergic agent for use in treating impaired neurological function as described herein. Treatment with L-dopa according to the invention is not according to the long term dosing regimens commonly employed for treating chronic neurodegenerative diseases, such as Parkinson's Disease. Accordingly, the doses useful in the invention for treating impaired neurological function associated with brain injury in an individual are generally much higher compared to initial treatments for Parkinson's Disease and for shorter durations (e.g., less than 24 months, see, above). This high-dose treatment using L-dopa is limited only by evidence of an acute untoward side effect that indicates a significant reason to reduce the dose in a particular brain injured individual. Accordingly, particularly useful doses of L-dopa include, without limitation, at least 1000, 1250, 1500, 1750, 2000, 2250, or 2500 mg/day. A particularly preferred dosage range for administering L-dopa to an individual according to the invention is from 1250 to 2500 mg/day.

As mentioned above with respect to apomorphine, high doses of L-dopa as described herein may also be administered to an individual according to the invention in conjunction with one or more compounds that provide additional therapeutic benefits. Such compounds include, without limitation, anti-emetic agents and/or other dopaminergic agents, including apomorphine. Again, combinations of apomorphine and L-dopa may or may not employ the high doses of L-dopa that are used in methods and compositions of the invention as the primary high potency dopaminergic agent. Still other compounds that are particularly useful in combination with high doses of L-dopa, as described herein, include compounds known to promote the half-life or absorption of L-dopa, such as decarboxylase inhibitors, catechol-O-methyltransferase (COMT) inhibitors, and combinations thereof. Preferred among decarboxylase inhibitors useful in the invention are those that inhibit L-dopa decarboxylase activity including, without limitation, carbidopa, bensarazide, and combinations thereof. Preferred COMT inhibitors useful in the invention include, without limitation, entacapone, tolcapone, and combinations thereof.

L-dopa is normally administered orally as a tablet or capsule form. Accordingly, it is also understood that in the embodiments of the invention wherein other compounds are used in conjunction with L-dopa, such other compounds may be administered to an individual in a mixture with L-dopa or separately, at the same or different (e.g., sequentially) time as administering L-dopa, and/or by the same or different route as used for administering L-dopa.

The methods and compositions of the invention may be used to treat impaired neurological function associated with a brain injury as manifested in an individual as any of a variety of altered consciousness state (ACS) disorders including, without limitation, coma, near-coma, vegetative state, persistent vegetative state, minimally conscious state, and the like. Such disorders are readily diagnosed and assessed using standard protocols of clinical neurology including, but not limited to, the Glasgow Outcome Scale, the Extended Glasgow Outcome Scale (GOS-E), the Kennedy Johnson Scale, the Disability Rating Scale, the Coma-Near Coma Scale, the Ranchos Amigos Scale, as well as standard neurological examination procedures that provide clinical impressions of change (CIC) in neurological function and, even, combinations thereof.

As mentioned with respect to apomorphine, the invention also provides methods for treating an impaired neurological function comprising administering to an individual an effective amount of L-dopa as described herein in conjunction with any of a variety of neurorehabilitation programs for restoring neurological function, including, but not limited to, physical protocols (exercises or tasks), sensory stimulation programs (e.g., using light, voice, pictures, tactile stimulation), electric and/or magnetic stimulation regimens (e.g., electroconvulsive therapy, transcranial magnetic stimulation (TMS), deep brain stimulation (DBS)), drug-based enhancement or stimulation regimens (e.g., using modafinil, caffeine, amphetamines), and combinations thereof.

DETAILED DESCRIPTION

Figure 1A:
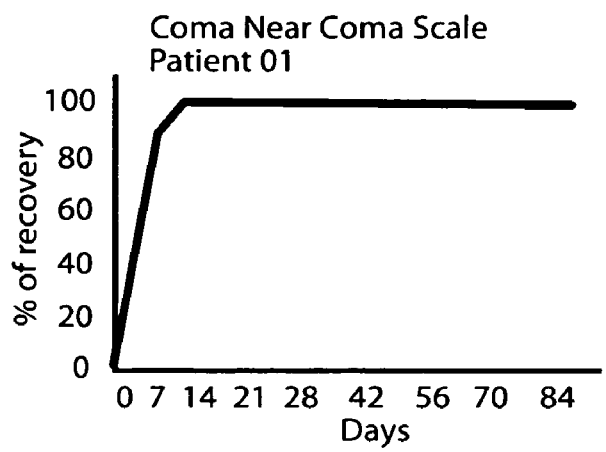
FIGS. 1A, 1B, and 1C show percent (%) recovery as a function of time (Days) for the altered consciousness state of Patients 01, 02, and 03 of traumatic brain injury when treated with apomorphine in a clinical study described in Example 2. Data were obtained using the Coma Near Coma (CNC) Scale that evaluates very early range of consciousness changes over time. See text for details.

This invention provides methods and compositions to treat impaired, i.e., diminished or lost, neurological function(s) in individuals who have sustained a brain injury, including injury from a traumatic brain injury or a stroke. In particular, the invention is based on the discovery that use of the highly potent dopaminergic agents, apomorphine or high doses of L-dopa (levodopa) as described herein, are particularly effective at treating impaired neurological function associated with a brain injury in an individual. Dopamine receptors are involved in neural transmission for a variety of neurological functions, including those functions that are commonly characterized neurologically as cognitive functions, motor functions, or as a combination of cognitive and motor functions. Apomorphine directly binds dopamine receptors to stimulate neural transmission, whereas L-dopa is metabolized to dopamine, which is the naturally occurring neural transmitter that binds dopamine receptors to stimulate neural transmission in the dopaminergic system.

In order that the invention may be more clearly understood, the following terms and abbreviations are used as defined below.

The term "brain injury" is a general term used to refer to a condition that results in central nervous system damage, irrespective of the physiopathological source. Among the most frequent origins of a "brain injury" are stroke and traumatic brain injury (TBI).

A "drug" refers to any compound or composition that has a pharmacological activity. Thus, a "therapeutic drug" is a compound or composition that can be administered to an individual to provide a desired pharmacological activity. For dopaminergic agents, such as apomorphine and high doses of L-dopa, as described herein, the desired pharmacological activity is stimulation of dopaminergic neural transmission to treat an undesired or harmful disorder or condition associated with brain injury in an individual. Such disorders or conditions include, but are not limited to, altered states of consciousness and/or other neurological impairments. A "prophylactic drug" is a compound or composition that can be administered to an individual to prevent or provide protection from the development in an individual of an undesired or harmful disorder or condition. A drug may have prophylactic as well as therapeutic uses. An "illicit drug" refers to a drug that is generally illegal to possess and/or use under any circumstances in a particular jurisdiction without governmental authority. Illicit drugs include illegal "recreational" and "addictive" compounds and controlled substances such as various opiates and various psychotropic substances.

"Neurological function" refers to a function of the body of an individual that requires normal functioning neural transmission. Neurological functions of an individual that may be impaired by brain injury, and that are therefore treatable according to this invention, include, without limitation, functions that are primarily sensory (e.g., light sensing, tactile sensing, hot-cold sensing), primarily cognitive (e.g., state of consciousness, memory, comprehension, reasoning), functions that are primarily based on motor activity (e.g., directed body movements, walking, maintaining balance), or a combination of (i.e., complex or integrated) neurological functions (e.g., speaking, writing, use of tools, operating machines). Impaired neurological functions may also be referred to by the name for the corresponding neurological disorder, a specific disorder for a particular state of less than normal consciousness (e.g., coma, near-coma, vegetative state, persistent vegetative state, minimally conscious state), and the like.

"Neurorehabilitation", as used herein, refers to any rehabilitation program that may be used for the purpose of improving, regaining, or restoring one or more neurological functions that may have been impaired (i.e., lost or diminished) in an individual as the result of a brain injury. Such neurorehabilitation programs comprise one or more neurostimuli designed to restore or improve one or more impaired neurological functions of the individual. Neurorehabilitation programs that may be used in conjunction with administering apomorphine and/or L-dopa as described herein include, without limitation, physical/sensory type stimulation protocols (exercises, tasks, light stimulation, voice stimulation, picture stimulation, tactile stimulation), electrical and/or magnetic stimulation regimens (e.g., electroconvulsive therapy, trans-cranial magnetic stimulation (TMS), deep brain stimulation (DBS); see, also, U.S. Pat. No. 6,463,328), and/or drug-based enhancement or stimulation regimens (e.g., using modafinil, caffeine, amphetamines). For example, a neurorehabilitation program may comprise having an individual who has sustained a brain injury perform or attempt to perform, often in multiple repetitions, one or more particular exercises or tasks designed to improve or restore one or more neurological functions. Thus, such exercises or tasks may include forms of physical therapy to promote development of an impaired motor function; exercises or tasks for improving aspects of cognitive functions as well, e.g., reading, recognition of objects, comprehension and response to commands, and the like; and exercises or tasks designed to improve a combination of motor and cognitive functions, e.g., speech, writing, operating machines, etc. The goal of neurorehabilitation is to improve or restore one or more neurological functions that were impaired due to brain injury in an individual and, thereby, advance the individual toward increased participation and independence in self-care, mobility, and/or employment. It is understood that neurorehabilitation applied to an individual in an altered state of consciousness may be greatly limited to tasks that promote an emergence to a state of greater consciousness, e.g., response to simple commands, directed eye or body movement, response to various stimuli. According to the invention, in its simplest form, neurorehabilitation of an individual who has sustained a brain injury and who is in an altered consciousness state (e.g., coma, etc.; see discussion infra) is a method comprising administering to the individual apomorphine or L-dopa as described herein and monitoring the individual for emergence to a state of greater awareness. Upon emergence to a higher or normal (or pre-injury) state of consciousness, the individual may then be administered apomorphine or L-dopa as described herein in conjunction with a neurostimulation program or regimen, as described above, designed to enhance or restore one or more neurological function(s) that remain impaired after the individual has emerged to a greater or normal state of consciousness.

Any of a variety of disorders or conditions may lead to the impairment of one or more neurological functions of an individual. Traumatic brain injury (TBI) and stroke are among the most frequently occurring and widely known events that can cause brain injury and an associated impairment of one or more neurological functions. Among the variety of causes of TBI diagnosed each year in the United States and around the world are vehicle accidents, such as involving a car, motorcycle, or bicycle, in which an impact to the head causes loss of consciousness and coma. TBI patients may partially emerge from a coma to some higher state of consciousness (e.g., near-coma, vegetative state, minimally conscious state), rarely to the point of fully recovered state of awareness, or, even with emergence to full consciousness, rarely with a full array of normal neurological functions (e.g., normal communication ability, motor ability, memory, senses, etc.).

A variety of rehabilitation programs are currently in use to promote restoration of various neurological functions impaired by brain injury, e.g., for TBI and stroke patients. Neurorehabilitation treatments according to the invention may comprise administering to an individual who has sustained a brain injury apomorphine or L-dopa at a dose of at least 1000 mg/day of L-dopa and one or more elements of a rehabilitation program currently used in the art to improve or regain neurological functions.

"Dopaminergic agent" or "dopaminergic compound" as used herein refers to a compound or composition that stimulates neurotransmission (signaling) through the dopaminergic system. Dopamine is the predominant catecholamine neurotransmitter in the mammalian brain. Neurotransmission through the dopaminergic system may occur by secretion of dopamine, inhibition of dopamine re-uptake, or by increasing synaptic concentrations of dopamine. Dopamine is involved in the control of a variety of neurological functions, including, but not limited to, cognition (e.g., consciousness, memory), motor activity (e.g., movement), emotion, positive reinforcement, food intake, and neuroendocrine regulation (see, e.g. Missale et al., *Physiol. Rev.,* 78: 189-225 (1998)). The dopaminergic system comprises at least five G protein-coupled dopamine receptor subtypes ($D_1$-$D_5$) that are widely expressed on cells of the central nervous system and also in certain locations in the periphery, such as in kidney, vasculature, and pituitary (Id.).

Two major categories of dopaminergic agents are dopamine receptor agonists, which are compounds that bind dopamine receptors and stimulate neural signaling via the dopaminergic system, and dopamine precursors, which are compounds that are metabolized to the active neurotransmitter dopamine, which in turn bind to dopamine receptors to cause transmission of a neural signal. A variety of dopamine receptor agonists are known and include, without limitation, apomorphine, bromocriptine, amantadine, pergolide, pramipexole, ropinirole, fenoldopam, cabergoline, rotigotine, lysuride, talipexale, 7-OH DPAT, quinpirole, and SKF-38393 (Id.). Dopamine agonists have traditionally been further categorized as ergot derivatives (e.g., bromocriptine, pergolide, lysuride, cabergoline) and nonergot derivatives (e.g., ropinirole, pramipexaole) (see, e.g., Zafonte et al., *J. Head Trauma Rehabil.,* 15: 1179-1182 (2000)).

The most widely used and best-known dopamine precursor is L-dopa (levodopa), which has been used in treating Parkinson's Disease, a disease characterized by dopamine depletion.

"Apomorphine" is a potent dopaminergic agent. It is a dopamine receptor agonist that binds directly to dopamine receptors (as opposed to metabolic agonists, such as L-dopa) and is reported to have a particularly high affinity for the $D_2$-like dopamine receptors (see, e.g., Missale et al., *Physiol. Rev.,* 78: 189-225 (1998)). Apomorphine binds to both groups of dopamine receptors: the $D_1$-like group ($D_1$ and $D_5$) and the $D_2$-like group ($D_2$, $D_3$, $D_4$) of receptors. Prior therapeutic uses of apomorphine have included to induce vomiting (emetic agent), to reduce the number and severity of "off" phases in certain patients with Parkinson's Disease that are refractory to conventional dopaminergic (L-dopa) therapy, and to treat male impotence (see, e.g., U.S. Pat. Nos. 6,306, 437 and 6,436,950).

Considered as among the most potent of dopamine agonists in the arsenal of drugs for treating Parkinson's Disease, use of apomorphine to a Parkinson's Disease patient is recommended after a clinical finding that a patient has failed to respond to or must be removed from other more widely used agents for treating Parkinson's Disease, notably, L-dopa, bromocriptine, amantadine, or other agents (Colosimo et al., *Clin. Neuropharmacol.,* 3: 243-259 (1994); Missale et al., *Physiol. Rev.,* 78: 189-225 (1998)).

Apomorphine is chemically described as (R)-5,6,6a,7-tetrahydro-6-methyl-4H-dibenzo[de,g]quinolin-10,11-diol (molecular weight 267). The CAS registry number of apomorphine hydrochloride, anhydrous, is 41372-20-7. The chemical structure of apomorphine as a neutral compound can be represented by the following formula:

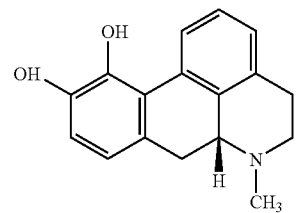

wherein only the stereochemically relevant hydrogen (at position 6a) is shown for structural clarity. The term "apomorphine", as used herein, encompasses not only a neutral free base form as in the above structure, but also individual stereoisomers and racemic mixtures thereof, pro-drug forms of apomorphine (i.e., compounds that are metabolized to apomorphine when administered to an individual), and any of a variety of salt forms of apomorphine, i.e., "acid addition salt" (or simply "acid salt") forms of apomorphine. The "acid" of an acid addition salt form of apomorphine may be inorganic (e.g., HCl) or organic (e.g., lactic acid, acetic acid). Preferably, apomorphine is used as the apomorphine hydrochloride salt. Such acid salt forms of apomorphine are particularly useful in pharmaceutically acceptable liquid (solutions, suspensions) compositions used to administer apomorphine to an individual. Use of obvious functional equivalents to the above structure, or chemically-modified equivalents of apomorphine, are also contemplated.

Apomorphine may be formulated for administration by a variety of routes, e.g., subcutaneously, sub-lingually (see, e.g., U.S. Pat. Nos. 5,770,606; 6,306,437), and nasally (see, e.g., U.S. Pat. No. 6,436,950). As discussed below, parenteral administration of apomorphine is particularly useful in methods of the invention, although other routes are not excluded. Apomorphine hydrochloride is generally the preferred, pharmaceutically acceptable, salt form employed for administering an effective amount of apomorphine to an individual according to the invention. Nevertheless, in addition to the hydrochloride salt form of apomorphine, other acid salt forms of apomorphine may be used in the invention including, but not limited to, a hydrobromide salt, a hydroiodide salt, a bisulfate salt, a phosphate salt, a lactate salt, a tartarate salt, a maleate salt, a succinate salt, a citrate salt, a gluconate salt, an acetate salt, and the like.

By "pharmaceutically acceptable" is meant a material that is not biologically, chemically, or in any other way, incompatible with body chemistry and metabolism and also does not adversely affect the desired, effective activity of a dopaminergic agent or any other component in a composition that may be administered to an individual to treat an impaired neurological function according to the invention.

"Consciousness" and "awareness" are, unless indicated otherwise, synonymous, and refer to the cognitive state of a person with respect to self and environment, consistent with usage by persons in the field of neurology. "Consciousness" has been technically defined as a spontaneously occurring state of awareness of self and environment comprising two dimensions, i.e., a "wakefulness dimension" (e.g., as evident by a circadian sleep cycle) and an "awareness dimension" (see, Ashwal, *Brain & Develop.*, 25: 535-545 (2003)). Normal consciousness (full awareness) requires arousal, which is an independent, autonomic-vegetative brain function subserved by ascending stimuli, emanating from the pontine tegmentum, posterior hypothalamus, and thalamus that activate mechanisms inducing wakefulness. Cerebral cortical neurons and corresponding reciprocal projections to and from the major subcortical nuclei subserve awareness. It is understood that an individual may have a discernable circadian sleep-wake cycle, as in a vegetative or minimally conscious state, but lack a normal awareness of self and environment.

The terms "altered consciousness state disorder", "altered consciousness state", "ACS", "severely altered consciousness", "severe alteration in consciousness", "severely altered consciousness state", and "SACS", as used herein (whether or not written in upper or lower case letters), are synonymous and refer to the broad group of primarily cognitive neurological disorders of the brain that describe an impaired state of consciousness and include any degree of unconsciousness of an individual such that the individual is unable to be aroused to and/or to maintain a normal state of awareness of self and/or environment at a level that permits the individual, except for any physical disability, to care for himself, i.e., to function in a state of normal consciousness.

Altered state of consciousness disorders comprise those diagnosed according to established neurological standards and methods known in clinical neurology for assessing the conscious state of patients of brain injury. ACS disorders as understood herein include, but are not limited to, the following disorders, listed from lower to higher (i.e., more emergent) state of consciousness: coma, near-coma, vegetative state, persistent vegetative state (PVS), and minimally conscious state (MCS). It is further understood that ACS disorders of concern for the methods and compositions described herein are those that are associated with a brain injury that is caused by undesired detrimental or pathological events, including, but not limited to, traumatic brain injury (TBI, e.g., head trauma from a fall or a vehicle accident), an ischemic event in an individual (blockage of normal blood flow anywhere in an individual resulting in brain injury, e.g., stroke), anoxic event (lack of oxygen to the brain), hypoxic oxygen event (lack of sufficient oxygen to the brain), drug-induced brain injury (e.g., alcoholic coma, heroin overdose, drug-associated locked-in disorder), and congenital or developmental brain disorders, such as lissencephaly). ACS disorders treated according to the invention do not include states of consciousness as might result during hypnosis or some other form of subliminal suggestion as might be employed to achieve a desired behavioral modification.

Traumatic brain injury (TBI) and stroke are among the most frequent and widely known causes of brain injury that often result in an ACS disorder. TBI includes penetrating (e.g., gunshot wound) and non-penetrating (e.g., strike to the head) forms of brain trauma. Among the variety of causes for the millions of cases of TBI diagnosed each year in the United States and around the world, one of the most frequent is a vehicle accident, such as involving a car, motorcycle, bicycle, in which an impact to the head causes loss of consciousness and coma. Depending on the degree of trauma, such TBI patients may partially emerge from a coma to some higher state of consciousness (e.g., near-coma, vegetative state, minimally conscious state), but rarely to the point of fully recovered state of awareness, and rarely with a full array of normal neurological functions (e.g., normal communication ability, motor ability, memory, senses, etc.).

"Coma" is a type of severely altered state of consciousness disorder characterized by a state of deep, unarousable (i.e., by normal stimuli), unresponsive, sustained, pathologic unconsciousness wherein the eyes are closed, and which results from dysfunction of the ascending reticular activating system either in the brainstem or in both the cerebral hemispheres (see, Ashwal, *Brain & Develop.*, 25: 535-545 (2003)). Coma is understood to indicate the ACS disorder of least awareness and deepest state of unconsciousness, except for death, of an individual that has sustained a brain injury. Among notable characteristics, an individual in a coma does not have a discernable circadian sleep-wake cycle and lacks auditory, visual, communicative, and emotional functions (see, e.g., Giacino et al., *Neurology*, 58: 349-352 (2002)). Temporally, diagnosis of coma usually requires the period of unconsciousness to persist for at least one hour to distinguish coma from syncope, concussion, or other states of transient unconsciousness (Id.). Individuals in a coma are unconscious because they lack both wakefulness and awareness dimensions (see, above).

"Near coma", as used herein, refers to a low state of consciousness that is, nevertheless, deemed more emergent in awareness than coma but less than vegetative state.

"Vegetative state", "VS", "persistent vegetative state", and "PVS", refer to the condition of complete unawareness of the self and the environment, but in contrast to coma, with sleep-wake cycles with complete or partial preservation of the hypothalamic and brain stem autonomic functions. Accordingly, a vegetative state is considered to be a more emergent state of consciousness than coma. The periods of wakefulness and sleeping of the vegetative state are typically irregular. In addition, when the eyes are opened, the individual fails to exhibit visual fixation or sustained visual tracking, and also may exhibit inconsistent head, trunk, and limb movements with respect to various stimuli (see, Ashwal, *Brain & Develop.*, 25: 535-545 (2003)). Vegetative state (VS) and persistent vegetative state (PVS) are usually distinguished in the art based on time course. Both VS and PVS are disorders in which the individual is considered to be in an unaware state that is, nevertheless, more emergent in awareness than coma, as evident by various characteristics such as eye opening or a discernible circadian sleep-wake cycle (see, e.g., Ashwal et al., *Brain Develop.*, 25: 535-545 (2003)). PVS is typically the designation when the individual has been in VS for more than a week (see, e.g., The Multi-Society Task Force on Persistent Vegetative State, *N. Eng. J. Med.*, 330: 1499-1508 (1994)).

"Minimally Conscious State" (MCS) is a relatively new designation for a defined altered consciousness state (see, e.g., Giacino et al., *Am. Acad. Neurol.*, 58: 349-353 (2002); Ashwal et al., *Brain Develop.*, 25: 535-545 (2003)). MCS is generally considered the most emergent of altered consciousness state disorders that currently may be assessed by clinical criteria (Id.) and is a more emergent state than vegetative state (see, Giacino et al., *Neurology*, 58: 349-353 (2002); Ashwal, *Brain & Develop.*, 25: 535-545 (2003)). As a relatively newly defined state, not all practitioners have acceded to the legitimacy of or necessity for this category, opting for degrees within other older categories. Yet, the distinction from vegetative state is based on criteria that provide definite behavioral evidence of an awareness, albeit very limited, of self or environment based on one or more of four classes of behaviors, i.e., simple command-following, gestural or verbal "yes/no" response (regardless of accuracy), intelligible verbalization, and non-reflexive, "purposeful" behaviors (Ashwal, *Brain Develop.*, 25: 535-545 (2003)). Functional interactive communication and use of extremities are considered key indications of further emergence from the minimally conscious state toward normal consciousness (Id.). Whether or not the "minimally conscious state" per se is ultimately incorporated into the clinical diagnostic jargon of neurology does not, however, detract from or otherwise affect the methods and compositions described herein for treating impaired neurological function; changes in a state or pattern of consciousness and/or any other neurological function are readily assessed by any of a variety of methods and scales employed in clinical neurology (see, below).

Phrases that refer to administering or the administration of a drug, compound, or procedure "in conjunction with" apomorphine or L-dopa as described herein are understood to refer to any combination of therapeutic methods, compositions, or procedures that encompasses co-administration (i.e., together, e.g., as in a solution, dispersion, or other mixture), concurrent administration (essentially at the same time), and sequential administration (before or after) of a drug, other composition, or rehabilitative procedure (e.g., a task or exercise for cognitive and/or motor function), in addition to the administration of the apomorphine or L-dopa as described herein. It is also understood that administration of a drug or other composition "in conjunction with" apomorphine or L-dopa according to the invention may comprise using the same or different route used to administer apomorphine or L-dopa to an individual.

Terms such as "parenteral", "parenterally", and the like, refer to routes or modes of administration of a compound or composition to an individual other than along the alimentary canal. Examples of parenteral routes of administration include, without limitation, subcutaneous (s.c.), intravenous (i.v.), intramuscular (i.m.), intra-arterial (i.a.), intraperitoneal (i.p.), transdermal (absorption through the skin or dermal layer), nasal or pulmonary (e.g., by inhalation or nebulization for absorption through the respiratory mucosa or lungs), direct injections or infusions into body cavities or organs, as well as by implantation into the body or connection to the body of any of any a variety of drug delivery devices (e.g., implantation of a time-release composition, depot, or device that permits active or passive release of a compound or composition into the body).

The terms "enteral", "enterally", "oral", "orally", "non-parenteral", "non-parenterally", and the like, refer to administration of a compound or composition to an individual by a route or mode along the alimentary canal. Examples of enteral routes of administration include, without limitation, swallowing solid or liquid forms, sub-lingual (absorption under the tongue), nasojejunal or gastrostomy tubes (into stomach), intraduodenal administration, as well as rectal administration (e.g., suppositories for release and absorption of a compound or composition by in the lower intestinal tract of the alimentary canal).

The meaning of other terms will be evident by the context of use and, unless otherwise indicated, are consistent with the meanings understood by those skilled in the fields of neurology and neurorehabilitation.

Assessment of Neurological Health

The neurological health, including state of consciousness and other neurological functions, of an individual who has sustained a brain injury is typically assessed and/or monitored by a neurologist or other skilled healthcare professional that employs one or more recognized diagnostic protocols or scales known in the art. Routine neurological examination procedures are known in clinical neurology for assessing motor function (e.g., body movement), cognitive function (e.g., consciousness, thinking, reasoning, memory, circadian sleep-wake rhythm), and "complex" neurological functions having motor and cognitive functions (e.g., speech, writing, problem solving, operating machines). Among such protocols are various scales that comprise a defined set of parameters or tasks that are conducted or administered by a trained practitioner to assess an individual's state of consciousness. Such scales for consciousness are highly useful in diagnosing neurological health as an assessment of a pattern or state of consciousness of an individual is typically deduced based on assessment of a variety of neurological functions, including not only cognitive functions (e.g., memory, circadian rhythm), but also motor functions (e.g., body and eye movements) and more complex functions that involve cognitive and motor functions (e.g., speech, response to commands). Such scales are particularly effective for tracking emergence from a lower state of awareness to a higher, more emergent, state, e.g., coma to PVS to MCS to full consciousness. Moreover, some scales may also permit discernment of changes in a pattern of consciousness and neurological functions that may take place within a particular ACS disorder. Thus, current scale procedures may permit a skilled practitioner to discern even subtle improvements in neurological function in an individual treated according to the invention. For example, it may be desirable to determine that progress, albeit slow, is being made within a particular altered consciousness state, or that improvement is being made in one function, such as communication, even if another neurological function, such as motor function, may not have been fully restored. Thus, observing a change in even a pattern of consciousness may become so significant as to eventually indicate a change to a higher (or lower) state of consciousness.

Examples of well-known, validated scales for assessing consciousness and other neurological functions include, but are not limited to, the Glasgow Outcome Scale, the Extended Glasgow Outcome Scale, the Kennedy Johnson Scale, the Disability Rating Scale, the Coma-Near Coma Scale, the Ranchos Amigos Scale, and standard neurological assessment protocols that provide clinical impressions of change. It is not uncommon for an assessment of consciousness and neurological health to use more than one of these scales, depending on the nature of the brain injury.

The Kennedy Johnson Scale, also known as Coma Recovery Scale (Giacino et al., *JFK Coma Recovery Scale and Coma Intervention Program Treatment Procedures*, (Center for Head Injuries, JFK Johnson Rehabilitation Institute, Edison, N.J., 1992); Giacino et al., *Arch. Phys. Med. Rehabil.*, 72: 897-901 (1991)), is a standardized method of assessment for grading the level of neurobehavioral responsiveness following severe brain injury. It is comprised of 25 items that assess the presence or absence of specific neurobehavioral signs that reflect the integrity of brain function. Responses are evaluated in the areas of arousal/attention, auditory function, visual function, motor function, motor/verbal ability, and communication. The Kennedy Johnson Scale yields six subscale scores and a total score. A total score between 0 and 14 is interpreted as coma or vegetative state and a score between 15 and 25 as emergent awareness. A disadvantage of this scale is that if a patient is unable to maintain arousal after stimulation, the assessment needs to be discontinued.

The Disability Rating Scale (DRS; Rappaport et al., *Arch. Phys. Med. Rehabil.*, 63: 118-123 (1982)) was originally developed and tested with older juvenile and adult individuals with moderate and severe traumatic brain injury. This scale evaluates midrange cognitive-motor changes and tracks an individual from coma to re-integration into the community. Various items in this scale address impairment, disability, and handicap. The DRS is a 31-point scale ranging from 0 (no disability) to 30 (death). Accordingly, the maximum score a living patient can obtain is 29 (extreme vegetative state) and 1 to 28 represent different grades of disability. A disadvantage of this scale is that it is relatively insensitive at the low end of the scale (i.e., mild traumatic brain injury). In particular, the scale does not have the ability to reflect very subtle, but sometimes significant, changes in an individual within a specific window of recovery.

The Coma/Near Coma (CNC) Scale evaluates very early range of consciousness changes over time and essentially expands the levels of the Disability Rating Scale (DRS) that incorporate the vegetative and extreme vegetative categories (i.e., DRS scores between 21 and 29) (see, e.g., O'Dell et al., *Neurorehabil.*, 6: 45-55 (1996); Pilon et al., *Brain Injury,* 10: 421-437 (1996); Rappaport et al., *Arch. Phys. Med. Rehabil.*, 73: 628-634 (1992); Talbot et al., *Brain Injury,* 8: 689-699 (1994)). The CNC scale has five levels: no coma, near coma, moderate coma, marked coma, and extreme coma.

The Glasgow Outcome Scale (GOS; see, Jennet and Bond, *Lancet,* 1: 480-484 (1975)) is another widely used scale for assessing severe brain damage. A further modification of the Glasgow Outcome Scale, i.e., the Extended Glasgow Outcome (GOS-E) Scale (Wilson et al., *J. Neurotrauma,* 15: 573-85 (1998)), has also found use in assessing consciousness and other neurological functions in individuals having an ACS disorder.

Of course, the most desired outcome of applying a treatment as described herein to an individual who has sustained a brain injury with an ACS disorder is the total emergence to normal functional awareness with restoration of all neurological functions at least to the level that existed prior to brain injury.

Use of High Potency Dopaminergic Agents

Dopaminergic potency of a compound may be assessed on the basis of affinity for binding to one or more dopamine receptors or any assay that permits measurement of a compound's ability to stimulate signaling through the dopaminergic system (Missale et al., *Physiol. Rev.,* 78: 189-225 (1998)). Dopaminergic potency may also be indicated by the effect a compound is observed to have on the brain, e.g., per unit dose.

This invention provides methods and compositions for treating one or a combination of impaired neurological functions in an individual who has sustained a brain injury comprising administering to the individual a high potency dopaminergic agent. The preferred high potency dopaminergic agent for use in the invention is apomorphine or relatively high doses (e.g., 1000 or more mg/day) of L-dopa. Apomorphine is classified as a highly potent dopamine agonist (Colosimo et al., *Clin. Neuropharmacol.,* 3: 243-259 (1994)) and is, therefore, useful in the compositions and methods of the invention. Prior therapeutic use of apomorphine as an emetic agent to induce vomiting is consistent with apomorphine's potent pharmacological effect upon the medullary chemoreceptors. More recently, apomorphine has been recommended for treating male impotency (see, e.g., U.S. Pat. Nos. 6,306,437 and 6,436,950) and for dystonia (see, e.g., Colosimo et al., *Clin. Neuropharmacol,* 17: 243-259 (1994)). The most common use for apomorphine continues to be as a replacement for L-dopa in treating Parkinson's Disease or as a treatment for severe motor fluctuations in Parkinson's Disease patients who have undergone chronic L-dopa therapy (Colosimo et al., *Clin. Neuropharmacol.,* 17: 243-259 (1994)).

In addition to its ability to bind the array of major dopamine receptors, apomorphine possesses pharmacological properties that distinguish this potent dopamine agonist over other compounds for use according to the invention. Of particular relevance here is the fact that apomorphine can be conveniently and easily prepared and administered to an individual by a parenteral route. Apomorphine has a low oral bioavailability because of extensive first pass hepatic metabolism, yet equilibrates quickly between the blood and tissues because of its high lipophilicity. In contrast to its poor bioavailability by oral administration, apomorphine is rapidly and completely absorbed when parenterally administered. Thus, apomorphine has a relatively quick onset of action when administered parenterally and is known to have a lower incidence of psychological effects than other dopaminergic agents (Lees et al., *Fund. Clin. Pharmacol.,* 7(3-4): 121-128 (1993)).

Moreover, parenteral administration of apomorphine and, indeed, other dopamine agonists, is particularly well suited for treating a brain-injured individual who may not be fully conscious (e.g., in a coma or other ACS disorder), because parenteral administration typically does not require active participation or cooperation by the brain-injured individual. Even if partially or fully emerged to a normal state of consciousness, such an individual may still lack sufficient neurological function to easily receive oral medications without mechanical intervention (e.g., gastrostomy or nasojejunal tubes). Accordingly, the benefits of parenteral administration of a dopamine agonist, such as apomorphine, that can be so formulated are most preferred for treating brain-injured individuals. Parenteral administration of a dopamine agonist to a brain-injured individual may be conveniently, routinely, and accurately provided by a healthcare provider using any of a variety of clinical devices and methods, e.g., by using a syringe device for single or multiple injections or by using a pump or device that provides a continuous, controlled infusion of the drug into the brain-injured individual. If the brain-injured individual shows progress in regaining or restoring one or more impaired neurological functions (e.g., by emergence to a higher or, most preferably, normal or pre-injury state of consciousness), parenteral delivery of a dopamine agonist may be continued, even in conjunction with an increasingly demanding neurorehabilitation program of cognitive and motor tasks or exercises. Routine clinical neurological assessments of the individual should be made by a trained healthcare provider in order to determine or conclude whether or not further administration of a dopamine agonist, with or without a continuing neurorehabilitation program, is likely to provide further progress in restoring an impaired neurological function. Such assessments for continuing, halting, or modifying a therapeutic regimen for brain-injured individuals are routinely performed by persons who are trained in clinical neurology and neurorehabilitation.

As discussed in more detail below, apomorphine is preferably administered to an individual by a parenteral route, e.g., subcutaneously such as through the abdominal wall in an area of high capillary flow. When administered subcutaneously, the plasma half-lives of apomorphine are approximately 15 minutes and 70 minutes, fitting a two compartment model of biodistribution (Nicolle, *Fund. Clin. Pharmacol.,* 7: 245-252 (1993)). The hydrochloride salt of apomorphine is a particularly useful form for preparing pharmaceutically acceptable solutions of apomorphine for parenteral administration to an individual according to the invention.

Apomorphine is rapidly and completely absorbed from subcutaneous tissues and is rapidly cleared. The effects of apomorphine are observed within five minutes following subcutaneous bolus administration. In the ACS patient, this rapid on and off allows better definition for a more exact onset of stimulation and duration of stimulation, which may be advantageous for many reasons, especially for inducing or maintaining a circadian rhythm in an ACS patient. Other types of agents having a longer half-life would continue to act on the CNS after termination of the infusion and would overlap with the sleep portion of the circadian cycle.

Therapeutic Methods and Compositions

As there are no recognized animal models for coma or any other disorder of altered consciousness state, the use and outcome of therapeutic methods and compositions for treating impaired neurological function associated with brain injury, including those described herein, are typically based on actual clinical studies of human patients. Often such studies are able to assess one or no more than a few patients, who have sustained brain injuries. Accordingly, new therapeutic uses for regulated and approved drugs, such as apomorphine and L-dopa, develop slowly and with intense interest by practitioners in the fields of clinical neurology and neurorehabilitation. Such data are now emerging in support for the methods and compositions described herein (see, Examples, below).

This invention provides methods and compositions for treating an impaired neurological function in an individual who has sustained a brain injury comprising administering to the individual apomorphine. This invention also provides methods and compositions for treating an impaired neurological function in an individual who has sustained a brain injury comprising administering to the individual high doses of the dopamine precursor L-dopa, preferably, a dose of at least 1000 or more mg/day of L-dopa. As discussed above, apomorphine is preferably administered to an individual by a parenteral route, e.g. subcutaneously, whereas L-dopa is routinely administered orally in any of the current commercially available tablet or capsule formulations.

A preferred dose of apomorphine that is administered to an individual is in the range of from 24 to 200 mg of apomorphine per day (mg/day) and, more preferably, in the range of from 48 to 128 mg/day. Daily dosing may be accomplished by single, multiple, or continuous injection or infusion of apomorphine into an individual. A preferred regimen for administering apomorphine to an individual according to the invention is to administer apomorphine at a rate of from 2 to 8 mg per hour for 12 to 16 hours. In a preferred aspect, apomorphine is administered in a manner to induce and mimic a normal circadian pattern in an individual in need of the same, the administration of apomorphine providing stimulation only during waking hours.

Commercially available preparations of apomorphine are typically provided at a concentration of 10 mg/ml. Subcutaneous administration of apomorphine at a concentration of 10 mg/ml is, however, not optimal as nodule formation (panniculitis) may occur at a site of injection. Accordingly, the concentration of a formulation of apomorphine administered by injection or infusion into an individual is preferably less than 10 mg/ml, e.g., 5 mg/ml.

L-dopa (levodopa) is commercially available in tablet or capsule form and thus universally administered orally for its known uses in chronic treatment of neurodegenerative diseases, such as Parkinson's Disease. Accordingly, a patient of brain injury that is unconscious or unable to swallow must receive current formulations of L-dopa through mechanical assistance, such as a gastrostomy tube, nasojejunal tube, and the like. Administration of L-dopa at a dose on the order of 1000 mg/day or greater is an exceptionally high dopaminergic composition compared to typical doses initially used treating, for example, Parkinson's Disease and, as such, serves as a high potency dopaminergic agent that is useful in the methods and compositions of the invention. A dose of 1000 mg/day of L-dopa is generally an acceptable starting point for treatments according to the invention, however, the invention also contemplates that even higher doses of L-dopa, such as at least 1250, at least 1500, at least 1750, at least 2000, at least 2500, or even higher amounts of milligrams of L-dopa per day may be safely administered to an individual according to the invention. Such a high daily dose of L-dopa may be advantageously achieved by administering to an individual multiple smaller doses (e.g., multiple administrations of one or more pills) that in sum will constitute a particular desired daily dose. Such doses of L-dopa generally may be well tolerated when administered to brain-injured individuals according to the invention to elicit emergence from an ACS disorder to a normal or pre-injury state of consciousness and/or to restore other impaired neurological functions associated with a brain injury. Only evidence of a significant, acute side effect need limit a particular dose of L-dopa of 1000 or more mg/day. A particularly useful range for administering L-dopa to an individual according to the invention is from 1250 to 2500 mg/day L-dopa. Such dosages for L-dopa are approximately 5 to 10-fold higher than those commonly employed in initial treatments for Parkinson's Disease, wherein treatments with L-dopa may continue for years and can lead to the development of counter-indicating and debilitating dyskinesias.

Dosing for a particular individual (patient) who has sustained a brain injury will be determined by the attending neurologist or other skilled healthcare provider taking into account a variety of clinical parameters that characterize that patient, e.g., state of consciousness, overall neurological condition, other injuries, cardiovascular condition, age, gender, weight, possible genetic factors, and the like. It is also understood that persons skilled in the art are aware that doses of pharmacologically active compounds, such as apomorphine and L-dopa, may be expressed not only in terms of mass (e.g., mg) of drug administered per day, but other units as well as, including, but not limited to, mg per kilogram (kg) of body mass, mg per surface area, mg per unit volume of formulation, and the like. As used herein, discussion of dosages in terms of mg/day refer to mg per patient per day and are based on the commonly used standard of a 70 kg male human patient. Similarly, discussion of dosing in terms of mg of compound per kg of body weight (mass) assume a 70 kg male human being. Hence, it is understood that when treating an individual that is more or less than 70 kg a dose may be appropriately modified in accordance with standard pharmacological adjustments. Thus, various examples of doses described herein are readily converted by persons skilled in the art to various other dosing units (and vice versa) required for treating specific individuals with particular pharmaceutically acceptable formulations.

The present invention provides a method of making a medicament for treatment of impaired neurological function of an individual who has sustained a brain injury comprising use of apomorphine or L-dopa to prepare such medicament. The medicament is used according to the invention to treat impaired neurological function. In addition to conventional or traditional means for administering apomorphine or L-dopa to an individual (e.g., syringes, pumps, lozenges, pills), a number of recently developed or emerging technologies may also be employed in methods of treating impaired neurological function according to the invention. For example, various delayed or slow release solid formulations of a desired compound may provide delivery of the compound to an individual over a specified period of time. In addition to conventional electric or mechanical powered pumps, a continuous infusion of a compound to an individual may be accomplished by using an implantable passive or osmotic pump that contains a desired compound(s) and is swallowed by or implanted into an individual in order to release a defined amount of the compound(s) into the body of an individual. Still other drug delivery systems useful in the methods of the invention may comprise a molecule-based or nano-technology that permits one, few, or several individual molecules of a desired compound to be encapsulated or otherwise sequestered for release at a particular site and/or time after being implanted in, injected into, inhaled by, or ingested by an individual. An example of a molecule-based technology that may be employed to deliver compounds according to the invention are $C60$, $C70$, $C76$, and/or $C80$ buckministerfullerenes. Fullerenes or other molecular structures may effectively sequester (without limitation as to mechanism) one or several individual molecules of a desired compound and permit release of those molecules in an individual at a single or multiple times throughout a desired dosing period.

Neurorehabilitation according to the invention may comprise administering apomorphine or L-dopa to an individual who has sustained a brain injury in conjunction with a protocol or regimen of neurostimulation that is designed to restore or improve an impaired neurological function. Such protocols or regimens may include, without limitation, physical/sensory type protocols, electric and/or magnetic stimulation regimens, and/or drug-based stimulation regimens. Preferably, apomorphine or L-dopa is administered prior to or simultaneously with applying a program to the individual or with having the individual perform or attempt to perform an exercise or task designed for improving or restoring a neurological function of the individual. Physical/sensory stimulation programs or protocols are particularly useful in the invention and may include any of the well-known methods employed in clinical neurology and neurorehabilitation to stimulate a response of from one or more of the five senses. Such methods may include applying, without limitation, one or more sensory stimuli such as light, color, a visual scene (e.g., a picture), hot or cold temperature, tactile stimulation (e.g., for surface feeling), a smell, a taste, a sound (e.g., a voice of a family member), and the like.

In addition, various methods are now available that provide electric or magnetic stimulation to the brain. Such methods, which may be used in conjunction with administering apomorphine or high doses of L-dopa as described herein, include, but are not limited to, vagal nerve stimulation, cranial nerve stimulation by electrical pulse waveform, neuromodulation using a pulsed electrical stimulus, electroconvulsive therapy, trans-cranial magnetic stimulation (TMS), deep brain stimulation (DBS), and the like.

While not intending to be bound by any particular mechanism, the methods of the invention for treating impaired neurological function associated with brain injury in an individual are intended to effectively and rapidly as possible increase neural transmission through the dopaminergic system to achieve one or more definite, observable, changes or endpoints, such as emergence from a lower to a higher state of consciousness, full arousal from unconsciousness to normal or pre-injury consciousness, and/or restoration of any other impaired neurological function associated with brain injury to the individual. In particular, the methods and compositions of the invention comprising apomorphine or high doses of L-dopa are not employed as chronic therapies as currently used to replace a progressive decline in the level of dopamine that characterizes neurodegenerative diseases, such as Parkinson's Diseases. Preferably, an apomorphine regimen or a high-dosage L-dopa regimen as described herein is applied continuously to an individual for no longer than 18 to 24 months, more preferably no longer than 12 to 18 months, more preferably no longer than 6 to 12 months, and most preferably 6 to 24 weeks. The dopaminergic agent is administered within the parameters discussed herein until an improvement in a neurological function or return to a normal pre-injury state of consciousness is achieved. It is also possible that a healthcare provider may elect to apply methods and compositions as described herein more than once to a particular individual, e.g., after some hiatus from therapy.

Alternatively, the dosage regimen may be designed with a particular emergent outcome in mind. For example, an important feature of coma patients is the absence of any evidence of circadian rhythm. Restoration of circadian rhythm is also a desired initial endpoint in the recovery from coma. Consequently, it is desirable to arrange for the treatment regimen of coma patients to have a daily duration corresponding to the approximately 16 waking hours of a normal daily sleep/wake cycle. This, combined with the fact that coma patients are unable in many cases to take medication orally, makes it highly advantageous to prescribe continuous medication for approximately 16 hours to induce a circadian rhythm. A 12 to 16-hour dose regimen frequently leads to restoration of circadian rhythm in a coma patient.

The methods and compositions described herein may be used to treat one or a combination of impaired neurological functions in an individual (patient) who has sustained a brain injury. In particular, it is understood that if a patient is diagnosed as having at least one, several, or multiple impaired neurological functions, the methods and compositions may be used according to the invention to treat even a single impaired function or a combination of impaired functions, i.e., even if another impaired neurological function is unknown or undiagnosed in the patient individual. An attending qualified healthcare provider (e.g., an attending physician) may have greater concern for or limited knowledge of only one or a particular combination of impaired neurological functions in a patient and, thus, employ compositions and methods described herein to treat that one or particular combination of impaired functions. For example, compositions and methods described herein may be used to treat a combination of an impaired motor function and an altered state of consciousness according to the invention, and not a particular impairment of speech or of memory such as amnesia, even if present in the patient or treatable by compositions or regimens already available in the art. Accordingly, the compositions and methods described herein include those that are used to treat a particular or a selected combination of impaired neurological functions of a patient.

Apomorphine or the high dosing with L-dopa described herein may advantageously also be administered to an individual in conjunction with any of a variety of other compounds that may provide one or more additional beneficial pharmacological activities. Such additional compounds may include, but are not limited to, an anti-emetic compound, another dopaminergic compound, an inhibitor of L-aromatic amino acid (L-dopa) decarboxylase activity, a catechol-O-methyltransferase (COMT) inhibitor, and combinations thereof. For example, some of the improvements made over the years for using L-dopa (levodopa) or other dopaminergic agents in chronic treatment regimens for Parkinson's Disease may also be applied in methods and compositions of the invention. Inhibitors of L-aromatic amino acid decarboxylase (also called L-dopa decarboxylase) and/or of catechol-O-methyltransferase (COMT) have been used to decrease degradation of extracerebral L-dopa. Thus, such inhibitors of enzyme activities that can degrade L-dopa may also provide an additional benefit of reducing acute side effects of L-dopa, such as nausea and vomiting. Examples of such useful inhibitors of L-aromatic amino acid decarboxylase activity include carbidopa and bensarazide. Useful COMT inhibitors include entacapone and tolcapone. Other anti-emetic agents that may be administered in conjunction with apomorphine or high doses of L-dopa according to the invention include, without limitation, prochlorperizine, trimethylbenzamide hydrochloride, chlormeprazine, prochlorpemazine, and combinations thereof. Pyridoxine may also be administered in conjunction with administration of L-dopa according to the invention.

As noted above, in addition to apomorphine, a variety of other dopamine agonists may also be included in the compositions and methods described herein. Such dopamine agonists, include, e.g., bromocriptine, amantadine, pergolide, pramipexole, ropinirole, fenoldopam, cabergoline, rotigotine, lysuride, talipexale, 7-OH DPAT, quinpirole, and SKF-38393; all of which have been shown to exhibit a pharmacological profile for binding to one or more of the major dopamine receptors $D_1$, $D_2$, $D_3$, $D_4$, and/or $D_5$, to stimulate dopaminergic signaling (see, e.g., Missale et al., *Physiol. Rev.*, 78: 189-225 (1998)). These dopamine agonists are less potent dopaminergic agents than apomorphine. The compositions and methods described herein comprising apomorphine or high doses (e.g., 1000 or more mg/day) of L-dopa may further comprise one or more of these other dopamine agonists, which may provide additional therapeutic activity, e.g., due to a different dopamine receptor binding profile, to enhance emergence toward full awareness and/or the restoration or improvement of neurological function(s) lost as the result of brain injury.

Methods of the invention to treat an impaired neurological function associated with brain injury in an individual may also comprise administering to the individual apomorphine or high doses of L-dopa, as described herein, in conjunction with one or more central nervous system enhancers or stimulants, such as, modafinil, methylphenidate, pemoline, caffeine, amphetamines, and combinations thereof.

Method of the invention for treating impaired neurological function in an individual who has sustained a brain injury may also comprise administering a combination of apomorphine and L-dopa to the individual. In such cases, the L-dopa and apomorphine are typically administered by separate modes of administration, e.g., apomorphine, parenterally; L-dopa, orally. In addition, when administered in combination with apomorphine, L-dopa may be administered in a dose that is less than that described above (i.e., <1000 mg/day) for treatments of impaired neurological function using L-dopa as a monotherapy. Such combinations may provide an additive or synergistic clinical response.

The handling of various dosage forms and techniques for administering compounds for use according to the invention will be within the skill and knowledge of practitioners familiar with pharmaceutical formulations comprising dopaminergic agents and other compounds.

More generally, compositions useful in the invention may be formulated for administration to an individual according to standard pharmaceutical protocols and texts (e.g., *Remington's Pharmaceutical Sciences*, 18th ed., Alfonso R. Gennaro, ed. (Mack Publishing Co., Easton, Pa. 1990)). Thus, in addition to apomorphine or L-dopa, compositions useful in the invention may also comprise any of a number of various pharmaceutically acceptable buffers (carriers), excipients, or adjuvants that may provide one or more beneficial pharmacological properties, including but not limited to, more efficient or less painful administration to an individual, more efficient delivery of dopaminergic agent(s) to the central nervous system, and/or longer storage of composition (e.g., preservative to enhance shelf-life, reducing agents). Accordingly, pharmaceutical compositions of this invention may include, without limitation, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Apomorphine compositions containing reducing agents such as sodium metabisulfite, ascorbic acid, and sodium ascorbate are also particularly contemplated.

Compositions according to the invention may be in the form of a sterile injectable preparation, such as a sterile injectable aqueous solution or an oleaginous suspension. Suspensions may be formulated according to techniques known in the art using suitable dispersing or wetting agents (e.g., an anionic detergent). A sterile injectable preparation may also be a sterile injectable solution or suspension in a non-toxic, parenterally acceptable diluent or solvent, such as a solution in 1,3-butanediol. Pharmaceutically acceptable aqueous buffer solutions that may be employed for parenteral administration of a compound or composition described herein include, without limitation, sterile water, physiological saline, bacteriostatic saline (e.g., saline containing about 0.9% benzyl alcohol), phosphate-buffered saline, Hank's solution, Ringer's-lactate and the like. In addition, sterile, fixed oils have been conventionally employed as a solvent or suspending medium for use in administering compositions. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this invention for oral administration may include, but are not limited to, capsules, tablets, caplets, pills, aqueous solution, oleaginous suspensions, syrups, or elixirs. In the case of tablets for oral use, carriers, which are commonly used include lactose and corn starch. Lubricating agents, such as magnesium stearate, may also be added. Capsules, tablets, pills, and caplets may also be formulated for delayed or sustained release. If desired, certain sweetening and/or flavoring and/or coloring agents may also be added.

For application topically, a composition of the invention may be formulated with a suitable ointment, gel, cream, or lotion containing the active components suspended or dissolved in a carrier. Carriers for topical administration include, but are not limited to, mineral oil, liquid petroleum, white petroleum, propylene glycol, polyoxyethylene polyoxypropylene compound, emulsifying wax and water. One or more emollients may be present to enhance penetration through the skin. Suitable carriers include, but are not limited to, mineral oil, sorbitan monostearate, polysorbate 60, cetyl esters wax, cetearyl alcohol, 2-octyldodecanol, benzyl alcohol and water. Topical administration may also be accomplished via transdermal patches or similar devices.

Compositions of this invention may also be administered in the form of suppositories for rectal administration. Such compositions can be prepared by mixing various desired pharmacologically active ingredients (e.g., dopaminergic agent(s), enzyme inhibitor(s), anti-emetic agent(s), etc.) with a suitable non-irritating excipient, which is solid at room temperature but liquid at body temperature and, therefore, will melt in the rectum space to release the active components that can be absorbed across the gut wall. Such materials include, but are not limited to, cocoa butter, beeswax and polyethylene glycols.

The pharmaceutical compositions of this invention may be administered nasally (intra-nasally, i.n.), in which case absorption of dopaminergic agent(s) may occur via the mucus membranes of the nose, or by inhalation or nebulization into the lungs (see, e.g., U.S. Pat. No. 6,436,950). Such modes of administration typically require that the composition be provided in the form of a powder, solution, or liquid suspension, which is then mixed with a gas (e.g., air, oxygen, nitrogen, etc., or combinations thereof) so as to generate an aerosol or suspension of droplets or particles. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

Pharmaceutical compositions of the invention may be packaged in a variety of ways appropriate to the dosage form and mode of administration. These include but are not limited to vials, bottles, cans, packets, ampoules, cartons, flexible containers, inhalers, and nebulizers. Such compositions may be packaged for single or multiple administrations from the same container. Kits, of one or more doses, may be provided containing both the composition in dry powder or lyophilized form, as well an appropriate diluent, which are to be combined shortly before administration. The pharmaceutical composition may also be packaged in single use pre-filled syringes or in cartridges for use in auto-injectors, needleless jet injectors, and automatic pumps that can be attached to the individual. Other kits provided by the invention may comprise apomorphine or L-dopa in combination with an appropriate delivery system. Such delivery systems may include, without limitation, external pumps, implantable pumps, metered dosage delivery devices, and the like.

Various antimicrobial agents may also be used in compositions of the invention to prevent degradation and contamination. Such commonly used antimicrobial agents included phenol, benzyl alcohol, meta-cresol, methyl paraben, propyl paraben, benzalconium chloride, benzethonium chloride, and EDTA. Such agents are present at concentrations that will prevent the growth of bacteria, fungi, and the like, but be non-toxic when administered to the intended individual.

Consistent with good manufacturing practices, which are in current use in the pharmaceutical industry and which are well known to the skilled practitioner, all components contacting or comprising the pharmaceutical agent (dopaminergic agent) must be sterile and periodically tested for sterility in accordance with industry norms. Methods for sterilization include ultrafiltration, autoclaving, dry and wet heating, exposure to gases such as ethylene oxide, exposure to liquids, such as oxidizing agents, including sodium hypochlorite (bleach), exposure to high energy electromagnetic radiation, such as ultraviolet light, x-rays or gamma rays, and exposure to ionizing radiation. Choice of method of sterilization will be made by the skilled practitioner with the goal of effecting the most efficient sterilization that does not significantly alter a desired pharmacological activity of the dopaminergic agent and other components of a composition intended for administration to an individual. Ultrafiltration is a particularly useful method of sterilization for pharmaceutical compositions that are aqueous solutions or suspensions.

In order to more fully illustrate the invention, the following non-limiting examples are provided.

EXAMPLES

Example 1

Emergence from Altered Consciousness State by Treatment with Elevated Levels of Levodopa (L-Dopa)

An open-label study was performed to evaluate the response of administering elevated doses of L-dopa (levadopa) to patients in a persistent vegetative state (PVS) or a minimally conscious state (MCS) following traumatic brain injury.

An analysis was made of five patients who had been in a persistent vegetative state or minimally conscious state for a mean of 47 days (range: 36-52 days), except for patients 5 and 6, who had been in a persistent vegetative state for 11 and 4 months, respectively. All patients were in a coma following a traumatic brain injury (TBI) due to a car accident. Patients were young adults ranging in age from 14 to 21 years old. The period of treatment was variable among patients according to clinical response, with a mean duration of 83 days.

The dopaminergic stimulation program in this study consisted of daily administration of levodopa/benserazide combination through gastrostomy or nasojejunal tube. The levodopa/benserazide combination is similar to the combination of levodopa and carbidopa, which is marketed in the United States as SINEMET® (Bristol Meyers Squibb, New York, N.Y.). Carbidopa or benserazide is usually administered in conjunction with levodopa to inhibit decarboxylase activity and to mitigate some side effects of administering levodopa alone. The initial dose of the levodopa/benserazide employed in this study was 125 mg QID, and the total amount administered varied according to clinical response (up to 1750 mg/day).

Sensory stimulation took place five days per week. Patient progress was assessed using two scales for assessing state of consciousness and neurological function. Both scales have been validated as clinical instruments. In each case, several evaluations were performed. The first evaluation took place immediately before initiation of treatment. Thereafter, assessments were made regularly over the course of the therapy, and the last when the patient was discharged from in-hospital. As patients progressed, they continued on ambulatory or daily-hospital rehabilitation programs, as there was no need for 24-hour nursing care. Patients also were videotaped at the beginning of the therapy and regularly over the course of the therapy.

The following scales for assessing state of consciousness and neurological function were employed in this study:
Kennedy Johnson Scale: The Kennedy Johnson Scale, also known as Coma Recovery Scale, is a standardized instrument for grading the level of neurobehavioral responsiveness following severe brain injury. It is comprised of 25 items that assess the presence or absence of specific neurobehavioral signs that reflect the integrity of brain function. Responses are evaluated in the areas of arousal/attention, auditory function, visual function, motor function, motor/verbal ability, and communication. The Kennedy Johnson Scale yields six sub-scale scores and a total score. A total score between 0 and 14 is interpreted as coma or vegetative state, and a score between 15 and 25 indicates emergent awareness. The disadvantage of this scale is that if the patient is unable to maintain arousal after stimulation, the assessment needs to be discontinued.
Disability Rating Scale: The Disability Rating Scale (DRS) was developed and tested with older juvenile and adult individuals with moderate and severe traumatic brain injury. This scale tracks an individual from coma to re-integration into the community. Various items in this scale address impairment, disability, and handicap. A person without disability would score 0. The maximum score a patient can obtain is 29 (extreme vegetative state), and a score of 1 to 28 represents different grades of disability. The disadvantage of this scale is that it is relatively insensitive at the low end of the scale (mild TBI). The scale does not have the ability to reflect very subtle, but sometimes significant, changes in an individual within a specific window of recovery.

Table 1 (below) shows the initial and final scores of the six patients on the DRS and Kennedy Johnson Scale (KJS) over the time of treatment. All six patients showed improvement on both scales.

TABLE 1

| | KJS | | DRS | | |
|---|---|---|---|---|---|
| Patient | Start | Last | Start | Last (as inpatient) | Last Score, after treatment (months from TBI) |
| 1 | 7 | 22 | 24 | 19 | 1 (18 months) |
| 2 | 7 | 24 | 24 | 14 | 5 (18 months) |
| 3 | 15 | 22 | 25 | 6 | 1 (16 months] |
| 4 | 8 | 22 | 25 | 5 | 5 (13 months) |
| 5 | 6 | 21 | 27 | 21 | 21 (26 months) |
| 6 | 11 | 24 | 23 | 14 | 14 (5 months) |

Table 2 (below) provides information on the age, number of days between injury and initiation of dopamine stimulation and number of days between starting of dopamine stimulation and clinical changes.

TABLE 2

| Patient | Age | Time from injury to initiation of treatment (days) | Time from initiation of treatment to change (days) |
|---|---|---|---|
| 1 | 16 | 52 | 3 |
| 2 | 20 | 64 | 8 |
| 3 | 18 | 36 | 14 |
| 4 | 21 | 37 | 10 |
| 5 | 19 | 319 | 40 |
| 6 | 14 | 127 | 21 |

Each case is examined in detail below.
Case 1

A male patient, age 16, suffered a severe traumatic brain injury (TBI) as a consequence of a motor vehicle accident. He was in a coma for 10 days, and then he remained in a minimally conscious state (MCS). He was admitted to the Rehabilitation Center 31 days after the accident. On day 52, dopaminergic stimulation treatment was started on a 125 mg intake, three times a day basis (375 mg daily) and, three days later, the patient started to follow verbal commands and progressively showed appropriate responses to different sensory stimuli. Dopaminergic stimulation was incrementally increased up to a 1000 mg per day (17 mg/kg/day) with acceptable tolerance and continuous improvement. Treatment was discontinued 45 days later. The DRS and Kennedy Johnson Scale (KJS) scores for this patient are shown in Table 3 (below). At discharge, he was able to talk and was independent in activities of daily living. He was able to return to and finish high school education.

TABLE 3

| Scores for Case 1. | | |
|---|---|---|
| Days After TBI | DRS | KJS |
| 34 | 24 | |
| 41 | 24 | 6 |
| 55 | 23 | 10 |
| 62 | 23 | 13 |
| 82 | 23 | 21 |
| 95 | 19 | 22 |
| 525 | 1 | |

Case 1

A female patient, age 20 years old, was admitted to the Intensive Care Unit due to severe TBI with signs of elevated intracranial tension. She remained in a pharmacological coma for 18 days. When sedating and relaxant medication was withheld, she remained in a vegetative state. She was transferred to the Rehabilitation Center on day 55 after the injury. She started to receive dopaminergic stimulation on day 64. Initial dose was 250 mg three times a days. After 8 days of treatment, the patient started to show visual fixation and tracking, and could move one arm willingly. Dose was progressively increased to a 1750 mg daily intake (37 mg/kg/day), which was well tolerated. Treatment lasted 90 days. Further improvement allowed her to be relatively independent and to take part in social activity (i.e. attends university). The DRS and Kennedy Johnson Scale scores for this patient are shown Table 4 (below).

TABLE 4

Scores for Case 2.

| Days After TBI | DRS | KJS |
| --- | --- | --- |
| 64 | 24 | 17 |
| 71 | 24 | 18 |
| 78 | 23 | 18 |
| 85 | 23 | 18 |
| 93 | 22 | 16 |
| 99 | 22 | 18 |
| 106 | 19 | 19 |
| 127 | 14 | 24 |
| 526 | 5 | |

Case 3

A female patient, age 18 years old, was admitted to the Intensive Care Unit due to severe TBI following a motor vehicle accident. She was sedated and treated for intracranial hypertension. When admitted to the Rehabilitation Center 30 days after the accident in a minimally conscious state. She showed spontaneous movements on the right side of the body, but these movements showed no functionality. On day 36, she was started on dopaminergic stimulation. The initial dose of 250 mg three times a day (750 mg daily) was gradually increased to 1000 mg daily dose (17 mg/kg/day) showing no side effects. Changes in her clinical status were observed after 14 days of treatment. She started to follow simple commands, showed visual fixation, and object tracking. Later, she improved her ability to communicate. Dopaminergic stimulation treatment was discontinued after 56 days, and she continued to improve. After treatment, she able to walk with crutches and is independent in the activities of daily living. The DRS and Kennedy Johnson Scale scores for this patient are shown in Table 5 (below).

TABLE 5

Scores for Case 3.

| Days After TBI | DRS | KJS |
| --- | --- | --- |
| 33 | 25 | |
| 43 | | 15 |
| 50 | 21 | 22 |
| 86 | 6 | |
| 160 | 2 | |
| 415 | 1 | |

Case 4

A 21-year old woman suffered a closed head injury in a motor vehicle accident. She was admitted to the Intensive Care Unit in a coma. Her clinical record showed she was in a vegetative state when dopaminergic stimulation was started 37 days after the accident. The initial dose was 250 mg every 8 hours (750 mg daily). Two days after initial intake, the patient prolonged vigil state. Five days after initiation, the dose was increased to 1000 mg per day and was progressively incremented to a 1500 mg daily dose (25 mg/kg/day), which was well tolerated. Ten days after initiation of treatment, the patient could be aroused more easily and sustained attention for more than 3 minutes. She also responded to different environmental stimuli. The patient received drug therapy for 60 days. Improvement occurred slowly and is still taking place. After treatment, the patient required assistance in the normal daily activities because of severe disability. However, she was aware of the environment, her own needs, and she could read and write. The DRS and Kennedy Johnson Scale scores for this patient are shown in Table 6 (below).

TABLE 6

Scores for Case 4.

| Days After TBI | DRS | KJS |
| --- | --- | --- |
| 47 | | 8 |
| 64 | 25 | 11 |
| 86 | | 14 |
| 110 | 24 | 11 |
| 144 | 21 | 17 |
| 162 | 15 | 22 |
| 270 | 5 | |
| 390 | 5 | |

Case 5

A 19-year-old man was admitted to the Rehabilitation Center on Sep. 30, 2002, after suffering a severe TBI in a motor vehicle accident on Nov. 11, 2001. During that prolonged period of time he remained in a coma due to severe neurological complications. Upon admission, he was immediately started on dopaminergic stimulation, 250 mg every 12 hours (500 mg per day), gradually increasing dose to 1000 mg daily (16 mg/kg/day). Twenty-five days after admission and the beginning of dopaminergic treatment, the patient was discharged respecting the family's will. Medication was not discontinued. Although medical follow-up was lost during that time, the family reported improvement, greater consistency in stimuli response, and a constant state of alertness since day 40. He returned as an outpatient 8 months later, and was assessed for improvement. He was aware of the environment and of his own needs. He voluntarily engaged in activities that interested him, and he helped with his personal care. He is still on dopaminergic stimulation treatment, 1000 mg per day. The DRS and Kennedy Johnson Scale scores for patient 5 are shown in Table 7 (below).

TABLE 7

Scores for Case 5.

| Days After TBI | DRS | KJS |
| --- | --- | --- |
| 319 | 27 | 6 |
| 329 | 27 | 11 |
| 353 | 27 | 11 |
| 589 | 21 | 21 |
| 780 | 21 | |

Case 6

A male patient, age 14 years old, suffered a severe traumatic brain injury (TBI) as a consequence of a motor vehicle accident. He was admitted to the Intensive Care Unit 52 days after injury took place with signs of elevated intracranial tension. He underwent a decompressive craniotomy. He remained in a coma for 36 days and emerged to a minimally conscious state. He showed spontaneous movements on the left arm but these movements were not functional. He had visual fixation to an object but object tracking was inconsistent. He started to receive dopaminergic stimulation on day 127 post injury and, although he had shown signs of improvement before treatment initiation, these signals were positively enhanced by medication as seen in the charts. Initial dose was 750 mg daily (19 mg/kg/day) and was not increased, as patient weighed only 88 pounds. Therapy continued for 40 days. At discharge, he was able to talk and move all extremities. The patient required assistance in the normal daily activities because of behavioral problems. The DRS and Kennedy Johnson Scale scores for Patient 6 are shown in Table 8.

TABLE 8

Scores for Case 6.

| Day After TBI | DRS | KJS |
|---|---|---|
| 53 | 23 | |
| 57 | | 11 |
| 78 | | 14 |
| 83 | 21 | |
| 108 | | 17 |
| 113 | 20 | |
| 115 | | 19 |
| 136 | | 24 |
| 140 | 14 | |

Analysis of Results

In all cases, the dopaminergic stimulation treatment employing elevated doses of a levadopa/bensarazide composition surprisingly yielded emergence to apparently normal awareness, albeit with or without full restoration of other neurological functions, as indicated by improved scale scores. All scores had stabilized before the beginning of treatment.

In contrast, previous therapies for ACS disorders have provided few if any indications of such emergence and rehabilitation as shown in this study. For example, prior to treatments as described herein, it has been reported that of patients remaining in a vegetative state one month after injury, 33% die, 15% remain in a PVS, 28% are severely disabled, 17% had moderate disability, and only 7% of such patients have been reported to attain a relatively good recovery (see, The Multi-Society Task Force on PVS, N. Engl. J. Med., 330: 1499-1508 (1994); The Multi-Society Task Force on PVS, N. Engl. J. Med., 330: 1572-1579 (1994)).

In the present examples, the mean interval of days between initiation of dopaminergic stimulation and the presence of consistent changes in the clinical status of the patients 1-5 was 15 days. The consistency of response to this pharmacological intervention contrasts to what is expected from the natural course of coma. Of the six patients admitted to this study, five emerged from post-traumatic coma caused by TBI. Such recovery, as measured by two independent scales, is surprising since it is substantially better than historical data.

In addition, treatment with dopaminergic stimulation was well tolerated, and no side effects were recorded in any patient.

The results of this open label trial study support the treatments described herein. Administration of dopaminergic agents to patients in a minimally conscious state or vegetative state yielded improved coma scores using two distinct scales. All six patients showed a positive response to potent dopaminergic stimulation. Five out of six patients in this study showed improved scores after an average of 15 days of treatment.

Example 2

Treatment by Subcutaneously Administered Apomorphine of Patients in Altered Consciousness State After Traumatic Brain Injury (TBI)

An open-label study was made of the safety and potential efficacy of apomorphine in accelerating recovery and improving the functional outcome of patients of post-traumatic brain injury vegetative state (VS) and minimally conscious state (MCS). The results of three patients who participated in this study are described below.

Apomorphine was administered in phases by the following protocols:

Titration Phase

The optimum apomorphine dose level was determined by a lead-in titration beginning at 2 mg/hour for 12 to 16 hours during the first day of infusion and escalating the dose in increments of 2 mg/hour every few days (e.g., Day 1: 2 mg/hour, Day 4: 4 mg/hour, Day 8: 6 mg/hour) until the maximum tolerated dose was reached. Apomorphine was administered subcutaneously via a needle connected to a specialized pump for at least 12 hours and no more than 16 hours a day.

Maintenance Phase

The patients received the maximum tolerated dose, 12 to 16 hours per day, for up to 84 days (or shorter or longer as indicated). If the patient developed an adverse event, the dose was reduced or eliminated, according to the opinion of the attending physician.

Prophylactic (Anti-Nausea Anti-Emetic) Pretreatment

To prevent side effects from dopaminergic stimulation (such as nausea), domperidone was administered starting 24-72 hours (h) prior to initiation of the drug therapy. Apomorphine treatment was initiated as soon as a patient was in a rehabilitation setting or the equivalent thereof and had received the prophylactic (anti-emetic, anti-emetic) pretreatment.

Sensory Stimulation

During exposure to apomorphine, all patients received a standardized program of sensory stimulation (or equivalent therapeutic regimen) once or twice a day.

Patient 01: Clinical History 25 year old male sustained traumatic brain injury (TBI) in a vehicular accident.

Intensive Care Unit patient for 3 weeks.

Intracranial hypertension and cranial decompression.

MRI: Diffuse Axonal Injury (DAI) grade II, frontal contusion.

Hypothalamic Dysautonomic Syndrome (fever, tachycardia, hypertension).

Fracture on left tibia that required external fixation.

Treated with methylphenidate, 15 mg/day, for 12 days, no response to treatment.

Treated with bromocriptine, 10 mg/day, for next 8 days, no response to treatment.

Treated with baclophen for spasticity, 10 mg qid, from date of commencement of methyl phenidate treatment up through Day 95.

Admitted to Fleni Rehabilitation Unit at approximately 10 weeks from accident.

Vegetative State: CNC=20 as determined 2 days after admission to Fleni Rehab Unit.
Baseline Measurements taken on 28 and 29 days after admission: CNC=20, DRS=21.
Informed consent signed by parents for participation in clinical study.

Patient 01: Apomorphine Dosing

Following a 3-day treatment with domperidone (60 mg/day), Patient 01 started apomorphine treatment at approximately 1-month since admission to Fleni (Day 1), 104 days post-TBI.

The dosing schedule was:
  Day 1: 2 mg/h over 16 hours
  Day 2: 4 mg/h over 16 hours
  Day 3: 6 mg/h over 16 hours
  Days 4-21: 8 mg/h over 16 hours/day
  Days 22-84: 6 mg/h for 12-14 hours/day
  Days 84-180: 2 to 4 mg/h for 12 hours/day.
  Day 180: treatment discontinued Patient 01: Safety Observations Dose escalation was well tolerated. ECG and clinical labs were monitored several times during the study and no abnormal values were reported. Sporadic penile erections were observed. Patient verbally denied nausea or discomfort. After 16 days at 8 mg/h dose, mild dyskinesias and hallucinations were observed. Following a dose reduction to 6 mg/h, the dyskinesias and hallucinations disappeared. Patient did not show any other side effects or sign of discomfort.

Patient 01: Efficacy Observations

Patient 01 had been in a stable minimally conscious state condition since he was admitted to the FLENI Rehabilitation Center, 35 days before starting apomorphine therapy.
Day 1: hours after initial dosing, patient moved right thumb to command.
Day 2: moved limbs on command and answered yes/no questions.
Day 3: Spoke by phone with brother and named four friends in his room.
Day 4: named objects and associated them with their function.
Day 5: oriented to physician's last name and name of the institution.
Day 7: patient scores CNC=2, DRS=13, GOS-E=3. Patient continued a steady improvement from Day 14 to Day 84. At Day 14, CNC=0, DRS=13, GOS-E=3.
Day 84: CNC=0, DRS=10, GOS-E=3. At Day 84, in an attempt to discontinue the treatment, it was observed that the patient regressed to an "off" state and therefore it was decided to continue with the therapy until Day 180 at a lower dose (2 to 4 mg/h for 12 hours per day).
Day 95: patient had a surgical procedure to attach an intrathecal pump for delivery of baclophen, in an attempt to reduce the spasticity in the patient's limbs. The baclophen titration lasted for approx. 30 days. During this time, the patient had a regression in his DRS score.
At the study termination of Day 180, the apomorphine treatment was discontinued. Patient scored: CNC=0, DRS=15 and GOS-E=3.

Patient 01: Additional Notes

On Day 18, the nurse forgot to operate the pump in the afternoon shift. The pump remained off for two hours and it was observed that the patient had a decrease in his awareness status. Following the reconnection of the pump, patient regained "on" status within 15 minutes.

Patient 02: Clinical History 41 year old female sustained traumatic brain injury (TBI) in vehicular accident.
ICU for 1 month.
D.A.I, brain edema, intraventricular hemorrhage, ICP monitoring.
RT frontal infarction (diagonal to the head of the Caudate Nucleus).
Small infarction—right basal ganglia.
Suspected lacunar infarction—pons.
Treated with clonazepam, 1 mg tid (three times/day), from approximately 4 to 11 weeks from accident.
Treated with sodium valproate, 400 mg bid (two times/day), from approximately 4-12 weeks from accident, then reduced to 300 mg bid (twice/day).
Treated with domperidone, 20 mg tid, from approximately 9-11 weeks from accident, then, reduced to 10 mg tid.
Admitted to Lowenstein ICU Unit 1 month after accident.
Vegetative State: CNC=36 at approximately 9 weeks after accident.
Baseline Measurements taken approximately 9 weeks after accident: CNC=36, DRS=26.
Informed consent signed by legal representative to participate in clinical study.

Patient 02: Apomorphine Dosing

Following a 5-day treatment with domperidone (60 mg/day), Patient 02 started apomorphine treatment at 70 days post-TBI (10 weeks since the accident) (Day 1 of trial). The apomorphine dosing schedule was:
  Day 1: 2 mg/h over 12 hours.
  Day 2: 4 mg/h over 12 hours.
  Days 3-4: 6 mg/h over 12 hours.
  Days 5: 8 mg/h over 12 hours/day.
  Days 6-46: 2 to 6 mg/h for 12 hours/day.

Patient 02: Safety Observations

Dose escalation was well tolerated. ECG and clinical labs were monitored several times during the study and no abnormal values were reported. An inflammatory reaction on the skin reaction was observed at 8 mg/h dose. Excessive salivation and teeth grinding was observed during the higher doses periods. Yawning and snoring were observed sporadically.

On Day 47, the patient suffered a severe subdural bleeding with intracranial hypertension and symptoms of substantial herniation. Dosing at that time was 2 mg/h. Dosing was interrupted and patient was transferred to the intensive care unit (ICU). Approximately 4 months from the accident, the patient died.

The fact that the hemorrhage occurred 47 days after initiation of the daily administration of the drug, and at a dose lower than the highest dose received also indicates a lack of connection between apomorphine and the hemorrhage that occurred. Moreover, delayed traumatic intracerebral hemorrhage in post TBI patients, without intervening symptoms, is a reported phenomenon in the medical literature (see, e.g., Kaplan et al., *Clin. Neurol. Neurosurg.*, 105(3): 153-155 (2003)). Nonetheless, apomorphine has never been associated with intracranial bleeding.

A survey of 434 patients who had been in a vegetative state for 1 month post TBI, 24% of such patients are expected to die within the following 6 months and 33% within 1 year (see, "The Multi-Society Task Force Report on Persistent Vegetative State. Medical aspects of the persistent vegetative state. Part II", *N. Engl. J. Med.*, 330: 1572-1579 (1994)).

A committee appointed by the Ethics Committee was established to determine the relationship between the bleeding and apomorphine administration. The committee concluded that there was no connection between the bleeding and the administration of apomorphine.

Patient 02: Efficacy Observations

An improvement in the patient's consciousness state was observed during the first two weeks of drug administration and maintained until the bleeding event. Spontaneous movement occurred on her right limbs, including grasping movements of the hand. Patient blinked when faced with an advancing stimulus. On Day 9, Patient 02 started to follow simple commands. The improvements were clearly seen by the staff and by the family. The CNC scores improved from 36 at baseline to 26 at Day 42.

Patient 03: Clinical History

A 30 year old female sustained a traumatic brain injury (TBI) in a vehicular accident.
Admitted to FLENI Rehabilitation Center.
Baseline Measurements taken approximately 6 weeks after accident: CNC=33, DRS=23, GOS-E=2.
Informed consent signed by legal representative for participation in clinical study.

Patient 03: Apomorphine Dosing

Following a 3-day treatment with domperidone (60 mg/day), Patient 03 started apomorphine treatment at approximately 6 weeks after accident (Day 1), 46 days post-TBI. The dosing schedule was:
Day 1: 2 mg/h over 12 hours
Day 2: 4 mg/h over 12 hours
Day 3: 6 mg/h over 12 hours
Days 4-84: 4-8 mg/h over 12-14 hours/day
Day 84: Treatment discontinued.

Patient 03: Safety Observations

Dose escalation was well tolerated. ECG and clinical labs were monitored several times during the study and no abnormal values were reported. Patient 03 presented events of agitation and fever. On April 20 (Day 38), patient 03 suffered a seizure. Patient 03 was transferred to the ICU, and treatment was discontinued. The treatment was reinstated 7 days after the discontinuation. The investigator noted that: "the possibility of a seizure disorder related to apomorphine is unlikely since the seizure occurred during the night when the patient had been off medication for 10 hours prior to the seizure. Moreover, apomorphine has never been associated with seizures."

Patient 03: Efficacy Observations

On Day 2, patient started to vocalize words. Patient steadily improved her awareness status during the first 8 weeks. On Day 62, Patient 03 started to clearly respond to commands, recognize family members, respond to her name and respond to her age. Scores improved from CNC=33, DRS=23, GOS-E=2 at baseline to CNC=8, DRS=21, and GOS-E=3 at Day 84. Patient 03 maintained her motor and cognitive improvements during the first attempt to discontinue drug on Day 84, therefore the drug was discontinued, and the patient was discharged.

Summary of Data for Patients 01, 02 and 03 in Apomorphine Open Label Study

The scores for Patients 01, 02, and 03 in the above-described apomorphine open label study are provided in Table 9 (below).

TABLE 9

Scores for Patients 01, 02, and 03 from Apomorphine Open Label Study

| Patient | | Day 0 | Day 7 | Day 14 | Day 21 | Day 28 | Day 42 | Day 56 | Day 70 | Day 84 | Day 180 |
|---|---|---|---|---|---|---|---|---|---|---|---|
| 01 | CNC | 20 | 2 | 0 | 0 | 0 | 0 | 0 | 0 | 0 | |
| | DRS | 21 | 13 | 13 | 12.5 | 12.5 | 12 | 10.5 | 10.5 | 10 | |
| 02 | CNC | 37 | 33 | 24 | 24 | 24 | | | | | |
| | DRS | 26 | 24 | 19 | 22 | 22 | | | | | |
| 03 | CNC | 33 | 22 | 18 | 12 | 12 | 16 | 16 | 12 | 8 | 0 |
| | DRS | 23 | 22 | 22 | 22 | 22 | 22 | 22 | 22 | 21 | 12 |

Figure 1B:
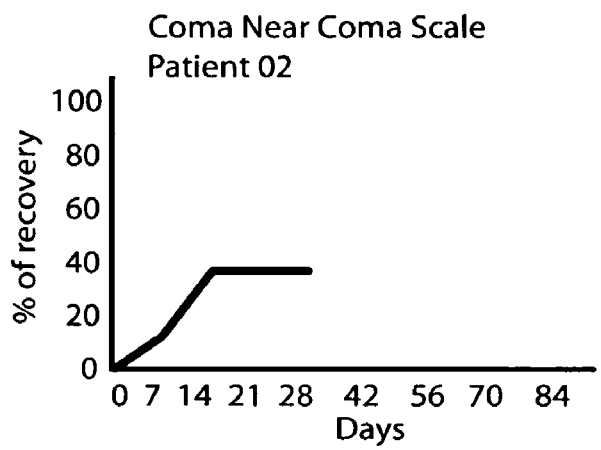
Figure 1C:
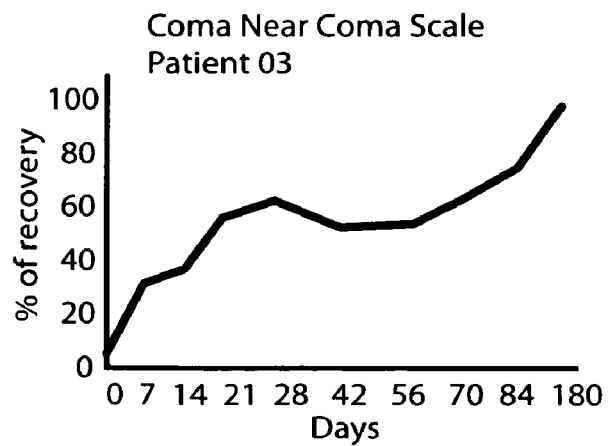
Figure 2A:
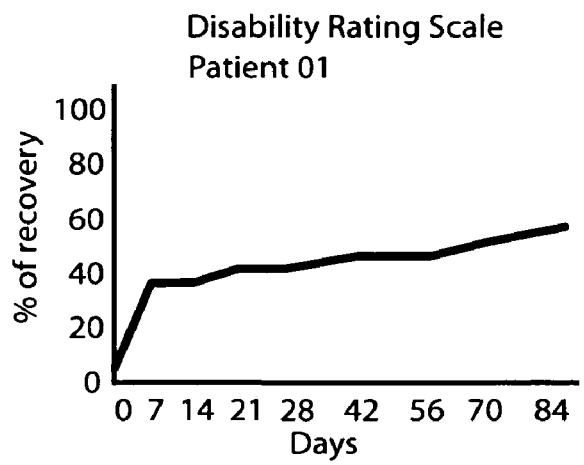
FIGS. 2A, 2B, and 2C show percent (%) recovery as a function of time (Days) for the altered consciousness state of Patients 01, 02, and 03 of traumatic brain injury when treated with apomorphine in a clinical study described in Example 2. Data were obtained using the Disability Rating Scale (DRS) that evaluates midrange cognitive-motor changes. See text for details.
Figure 2B:
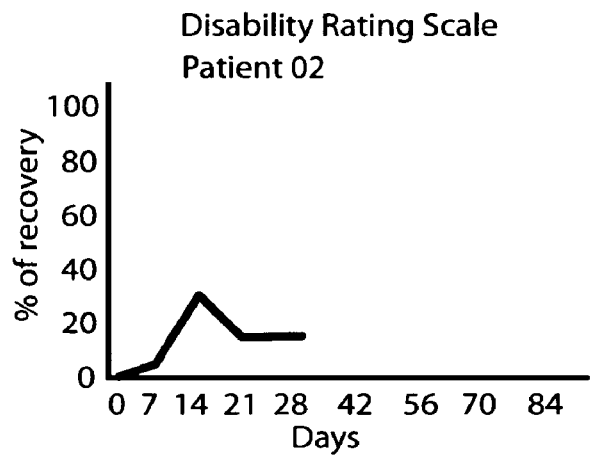
Figure 2C:
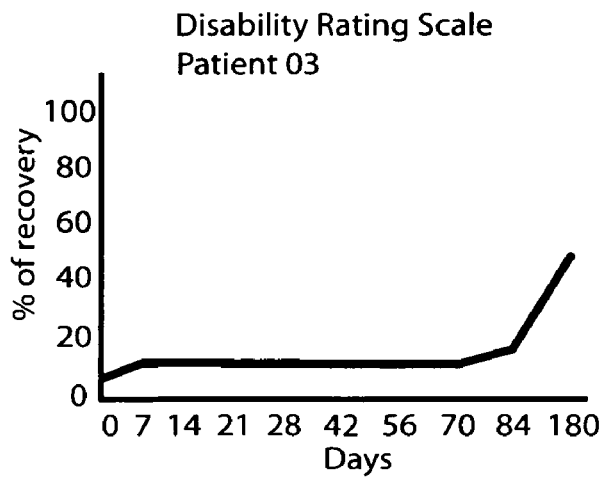

The above CNC and DRS data for each patient in this study are also shown as percent recovery over time (days) in FIGS. 1A-1C and 2A-2C, respectively.

The data indicate that apomorphine was effective at improving the altered consciousness state of patients who sustained a traumatic brain injury. Following this treatment, the patients showed improvement in coma scores.

All patents, applications, and publications cited in the above text are incorporated herein by reference.

Other variations and embodiments of the invention described herein will now be apparent to those of skill in the art without departing from the disclosure of the invention or the coverage of the claims to follow.

The invention claimed is:

1. A method of treating an altered consciousness state (ACS) in an individual who has sustained a traumatic brain injury comprising administering to said individual an effective amount of apomorphine.

2. The method according to claim 1, wherein said altered consciousness state is an ACS disorder.

3. The method according to claim 2, wherein said ACS disorder is selected from the group consisting of coma, near-coma, vegetative state, persistent vegetative state, and minimally conscious state.

4. The method according to claim 2, wherein said individual is administered apomorphine in an amount and for a period sufficient to stimulate an improvement in a pattern of consciousness within an altered consciousness state or in a change from a lower to a higher state of consciousness.

5. The method according to claim 4, wherein said improvement is indicated by improvement in a neurological function selected from the group consisting of circadian rhythm, eye opening, directed eye movement, directed body movement, response to verbal commands, communication ability, response to sensory stimulation, and combinations thereof.

6. The method according to claim 4, wherein said improvement is a change from a lower to a higher state of consciousness.

7. The method according to claim 6, wherein said higher state of consciousness is the state of full consciousness.

8. The method according to claim 4, wherein said improvement in a pattern or state of consciousness is determined using a protocol selected from the group consisting of Glasgow Outcome Scale, Extended Glasgow Outcome Scale (GOS-E), the Kennedy Johnson Scale, the Disability Rating Scale, the Coma-Near Coma Scale, Ranchos Amigos Scale, clinical impressions of change, and combinations thereof.

9. The method according to claim 1, wherein said apomorphine is administered to said individual by a parenteral route.

10. The method according to claim 9, wherein said parenteral route is selected from the group consisting of a subcutaneous route, an intravenous route, an intramuscular route, a transdermal route, a nasal route, and an inhalation route.

11. The method according to claim 9, wherein said apomorphine is administered to said individual by a parenteral route in a single dose using a syringe device or in a continuous infusion using a pump.

12. The method according to claim 1, wherein said apomorphine is administered to said individual by an enteric route along the alimentary canal.

13. The method according to claim 12, wherein said enteric route is selected from the group consisting of oral administration, sublingual administration, administration to the stomach by a tube, and rectal administration.

14. The method according to claim 1, wherein said brain injury is the result of an event selected from the group consisting of traumatic brain injury (TBI), a hypoxic event, an anoxic event, an ischemic event, organ failure, and a drug-induced brain injury.

15. The method according to claim 14, wherein said ischemic event is a stroke.

16. The method according to claim 14, wherein said TBI is the result of a fall on a surface or a vehicle accident.

17. The method according to claim 1, wherein said individual is administered apomorphine for a period sufficient to promote an improvement in the functional independence of the individual.

18. The method according to claim 17, wherein said improvement in the functional independence of said individual is indicated by improved communication ability, improved motor ability, improved ability for daily self care, and combinations thereof.

19. The method according to claim 1, further comprising administering to said individual an additional dopaminergic agent, selected from the group consisting of L-dopa, bromocriptine, amantadine, pergolide, pramipexole, ropinirole, fenoldopam, cabergoline, rotigotine, lysuride, talipexale, 7-OH DPAT, quinpirole, SKF-38393, and combinations thereof.

20. The method according to claim 19, wherein said additional dopaminergic agent is L-dopa.

21. The method according to claim 20, wherein said L-dopa is administered at a dose that is less than 1000 mg/day.

22. The method according to claim 1, wherein said apomorphine is administered in conjunction with an anti-emetic agent selected from the group consisting of domperidone, prochlorperizine, trimethobenzamide hydrochloride, chlormeprazine, prochlorpemazine, and combinations thereof.

23. The method according to claim 22, wherein said anti-emetic agent is domperidone.

24. The method according to claim 1, wherein said apomorphine is a single stereoisomer.

25. The method according to claim 1, wherein said apomorphine is a racemic mixture of stereoisomers.

26. The method according to claim 1, wherein said apomorphine is an acid salt.

27. The method according to claim 26, wherein said acid is selected from the group consisting of HCl, HBr, acetic acid, and lactic acid.

28. The method according to claim 26, wherein said apomorphine is apomorphine hydrochloride.

29. The method according to claim 1, wherein said apomorphine is administered to said individual in conjunction with an additional compound selected from the group consisting of pemoline, caffeine, amphetamines, modafinil, methylphenidate, and combinations thereof.

30. The method according to claim 1, wherein said apomorphine is administered to said individual in combination with applying to said individual at least one sensory stimulus.

31. The method according to claim 30, wherein said sensory stimulus is selected from the group consisting of light, color, a visual scene, hot temperature, cold temperature, tactile stimulation, a smell, a taste, a sound, and combinations thereof.

32. The method according to claim 1, wherein said apomorphine is administered to said individual in conjunction with a procedure to provide electric and/or magnetic stimulation to the brain, said procedure selected from the group consisting of vagal nerve stimulation, cranial nerve stimulation by electrical pulse waveform, neuromodulation using a pulsed electrical stimulus, electroconvulsive therapy, transcranial magnetic stimulation (TMS), deep brain stimulation (DBS), and combinations thereof.

33. The method according to claim 1, wherein said apomorphine is administered to said individual in conjunction with having said individual perform or attempt to perform a task or exercise to restore an impaired neurological function.

34. The method according to claim 1, wherein said apomorphine is administered to said individual in an amount of 12 to 200 mg/day.

35. The method according to claim 1, wherein said apomorphine is administered to said individual in an amount of 48 to 128 mg/day.

36. The method according to claim 34, wherein said amount of apomorphine is administered to said individual over a period of 12 to 16 hours/day.

37. The method according to claim 19, wherein said additional dopaminergic agent is capable of crossing the blood brain barrier.

38. The method according to claim 19, wherein said additional dopaminergic agent is administered to said individual by a parenteral or an enteric route.

39. The method according to claim 38, wherein said enteric route is via a nasojejunal tube or a gastrostomy tube.

40. The method according to claim 22, wherein said apomorphine is co-administered, concurrently administered, or sequentially administered with said anti-emetic agent.

41. The method according to claim 40, wherein said apomorphine is sequentially administered after administration of said anti-emetic agent.

42. A kit comprising apomorphine in one or more containers adapted for use in a pump for continuous infusion of said apomorphine and instructions for administering apomorphine by continuous infusion with a pump to treat an altered consciousness state (ACS) in an individual who has sustained a traumatic brain injury.

43. The kit according to claim 42, further comprising said pump for administering said apomorphine in said one or more ampoules to said individual.

* * * * *

UNITED STATES PATENT AND TRADEMARK OFFICE
CERTIFICATE OF CORRECTION

| | | |
|---|---|---|
| PATENT NO. | : 7,943,632 B2 | Page 1 of 1 |
| APPLICATION NO. | : 11/240281 | |
| DATED | : May 17, 2011 | |
| INVENTOR(S) | : Katzman et al. | |

It is certified that error appears in the above-identified patent and that said Letters Patent is hereby corrected as shown below:

At column 34, line 61, delete "ampoules" and insert --containers-- therefor.

Signed and Sealed this
Sixteenth Day of August, 2011

David J. Kappos
*Director of the United States Patent and Trademark Office*